(12) United States Patent
Akabane et al.

(10) Patent No.: US 9,890,252 B2
(45) Date of Patent: Feb. 13, 2018

(54) SILICONE COMPOUND AND COSMETIC CONTAINING THEREOF

(71) Applicant: SHIN-ETSU CHEMICAL CO., LTD., Tokyo (JP)

(72) Inventors: Emi Akabane, Annaka (JP); Tomoyuki Goto, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/334,355

(22) Filed: Oct. 26, 2016

(65) Prior Publication Data
US 2017/0137574 A1 May 18, 2017

(30) Foreign Application Priority Data

Nov. 16, 2015 (JP) ................................. 2015-224044

(51) Int. Cl.
| C07F 7/04 | (2006.01) |
|---|---|
| C08G 77/18 | (2006.01) |
| A61K 8/893 | (2006.01) |
| A61Q 19/00 | (2006.01) |
| C08G 77/46 | (2006.01) |
| C08G 77/50 | (2006.01) |
| C08G 77/00 | (2006.01) |

(52) U.S. Cl.
CPC .............. C08G 77/18 (2013.01); A61K 8/893 (2013.01); A61Q 19/00 (2013.01); C08G 77/46 (2013.01); C08G 77/50 (2013.01); C08G 77/70 (2013.01)

(58) Field of Classification Search
CPC ......... C08G 77/00; A61K 8/893; A61Q 19/00
USPC ...................................................... 556/445
See application file for complete search history.

(56) References Cited

U.S. PATENT DOCUMENTS

| 4,698,178 A | 10/1987 | Huttinger et al. |
|---|---|---|
| 6,576,623 B1 | 6/2003 | Nakanishi et al. |
| 2013/0046028 A1 | 2/2013 | Deeth et al. |
| 2015/0059102 A1* | 3/2015 | Souda ..................... D21C 9/02 |
| | | 8/137 |

FOREIGN PATENT DOCUMENTS

| JP | S61-90732 A | 5/1986 |
|---|---|---|
| JP | S61-293903 A | 12/1986 |
| JP | S61-293904 A | 12/1986 |
| JP | S62-187406 A | 8/1987 |
| JP | S62-215510 A | 9/1987 |
| JP | S62-216635 A | 9/1987 |
| JP | 3724988 B2 | 12/2005 |
| JP | 2013-525452 A | 6/2013 |
| WO | 2011/137212 A1 | 11/2011 |
| WO | 2013/029764 A2 | 3/2013 |

OTHER PUBLICATIONS

Mar. 21, 2017 Extended European Search Report issued in Patent Application No. 16002420.4.

* cited by examiner

*Primary Examiner* — Sudhakar Katakam
*Assistant Examiner* — Kofi Adzamli
(74) *Attorney, Agent, or Firm* — Oliff PLC

(57) ABSTRACT

The present invention provides a silicone compound shown by the formula (1) and having a weight-average molecular weight in the range of 500 to 200,000, $R^1_a R^2_b R^3_c R^4_d SiO_{(4-a-b-c-d)/2}$ (1), wherein $R^1$ represents the same or different organic group, $R^2$ represents a polyoxyalkylene group shown by $-C_m H_{2m}-O-(C_2 H_4 O)_g (C_3 H_6 O)_h R^6$, $R^3$ represents a branched type monovalent organosiloxane group shown by the following general formula (4), $M_o M^R_p D_q D^R_r T_s T^R_t Q_u$ (4), and $R^4$ represents a monovalent organosiloxane group shown by the following general formula (5) or the general formula (6), $MM^R D_{v-1}$ (5), $M_w D_{v-1} D^R_{v-2} T^R_{v-3}$ (6). This provides a silicone compound which has excellent emulsification ability and emulsion stability to silicone oil, and can secure high temporal stability.

8 Claims, No Drawings

SILICONE COMPOUND AND COSMETIC CONTAINING THEREOF

TECHNICAL FIELD

The present invention relates to a novel silicone compound and a cosmetic containing thereof.

BACKGROUND ART

Various oil materials such as silicone oil, ester oil, hydrocarbon oil are used for cosmetics. They are used depending on their characteristics and the purpose. For example, silicone oil has characteristics such as good usability including a light feeling and non-stickiness, excellent water repellency, and high safety. Each of these oil materials is blended in cosmetics solely or in a combined form.

In emulsion type cosmetics blended with oil materials and water, surfactant is generally used. When the oil material is silicone oil, it is difficult to obtain an emulsion with good stability even though an emulsifier such as polyoxyalkylene fatty acid ester is used. Accordingly, it has been proposed a method to use polyoxyalkylene modified organopolysiloxane (polyether modified silicone), which has good compatibility with silicone oils (PATENT LITERATURE 1 to PATENT LITERATURE 5).

In order to enhance the compatibility with oils, including not only silicone oil but also other oil materials, it has also been proposed a method to use organopolysiloxane having a long-chain alkyl group and a polyoxyalkylene group as well as straight chain silicone as an emulsifier (PATENT LITERATURE 6 and PATENT LITERATURE 7). The emulsified composition containing silicone oil or other oil materials, however, still have a problem for providing excellent emulsion stability and ensuring temporal stability. Moreover, emulsified cosmetics blended with polyether modified silicone still suffer from stickiness after being applied, and needs to achieve affective emulsifying property in a smaller blending amount.

In addition, in the case that powders are included in a cosmetic, it is necessary that the powders have excellent dispersion stability without causing changes such as agglomeration of powders. Alternatively, a polyether-modified silicone which has a dendrimer-like branched silicone structure has been known, but the structure of the dendrimer silicone moiety is so unique that a complicated process is necessary in its preparing process, and this causes higher production cost. Moreover, this polyether-modified silicone is difficult to obtain as a single product, and has lower reactivity due to its bulky structure (PATENT LITERATURE 8).

CITATION LIST

Patent Literature

PATENT LITERATURE 1: Japanese Patent Laid-Open Publication (Kokai) No. S61-293903
PATENT LITERATURE 2: Japanese Patent Laid-Open Publication (Kokai) No. S61-293904
PATENT LITERATURE 3: Japanese Patent Laid-Open Publication (Kokai) No. S62-187406
PATENT LITERATURE 4: Japanese Patent Laid-Open Publication (Kokai) No. S62-215510
PATENT LITERATURE 5: Japanese Patent Laid-Open Publication (Kokai) No. S62-216635
PATENT LITERATURE 6: Japanese Patent Laid-Open Publication (Kokai) No. S61-90732
PATENT LITERATURE 7: Japanese Patent No. 3724988
PATENT LITERATURE 8: Japanese Patent Laid-Open Publication (Kohyo) No. 2013-525452

SUMMARY OF INVENTION

Technical Problem

The present invention was accomplished in view of the above-described problems. It is an object of the present invention to provide a silicone compound which has excellent emulsification ability and emulsion stability to silicone oil, and can secure high stability with the passage of time.

Solution to Problem

To solve the foregoing problem, the present invention provides a silicone compound shown by the following average composition formula (1) and having a weight-average molecular weight in the range of 500 to 200,000, $$R^1_a R^2_b R^3_c R^4_d SiO_{(4-a-b-c-d)/2} \quad (1)$$

(wherein "a", "b", "c", and "d" each represent a number satisfying $1.0 \leq a \leq 2.5$, $0.001 \leq b \leq 1.5$, $0.001 \leq c \leq 1.5$, and $0 \leq d \leq 1.0$;

$R^1$ represents the same or different organic group selected from an alkyl group having 1 to 30 carbon atoms, an aryl group, an aralkyl group, a fluorine-substituted alkyl group, and an organic group shown by the general formula (2) —$C_l H_{2l}$—O—$R^5$, (in the formula, $R^5$ represents a hydrogen atom, a hydrocarbon group having 4 to 30 carbon atoms, or an organic group shown by $R^9$—(CO)—; $R^9$ represents a hydrocarbon group having 1 to 30 carbon atoms; and "l" represents an integer satisfying $0 \leq l \leq 15$);

$R^2$ represents the same or different polyoxyalkylene group shown by the general formula (3) —$C_m H_{2m}$—O—$(C_2H_4O)_g$$(C_3H_6O)_h R^6$, (in the formula, $R^6$ represents a hydrogen atom, a hydrocarbon group having 1 to 30 carbon atoms, or an organic group shown by $R^9$—(CO)—; $R^9$ has the same meaning defined above; and "g" and "h" each represent an integer satisfying $2 \leq g \leq 200$, $0 \leq h \leq 200$, and g+h is 3 to 200; and "m" represents an integer satisfying $1 \leq m \leq 15$);

$R^3$ represents the same or different branched type monovalent organosiloxane group shown by the following general formula (4), $$M_o M^R_p D_q D^R_r T_s T^R_t Q_u \quad (4)$$

(in the formula, $M=R^7_3 SiO_{0.5}$, $M^R=R^7_2 R^8 SiO_{0.5}$, $D=R^7_2 SiO$, $D^R=R^7 R^8 SiO$, $T=R^7 SiO_{1.5}$, $T^R=R^8 SiO_{1.5}$, and $Q=SiO_2$; $R^7$ represents the same or different organic group selected from an alkyl group having 1 to 30 carbon atoms, an aryl group, an aralkyl group, and a fluorine-substituted alkyl group; $R^8$ represents an organic group shown by —$C_n H_{2n}$—; "n" represents an integer satisfying $1 \leq n \leq 5$; "o" represents an integer of 1 or more; "q" and "s" each represent an integer of 0 or more; "p", "r", "t", and "u" each represent 0 or 1; with the proviso that "s", "t", and "u" are not equal to 0 at the same time, the sum of "p", "r", and "t" is 1, and when q=0, "o" is 2 or more and the sum of "s" and "u" is 1 or more);

$R^4$ represents the same or different monovalent organosiloxane group shown by the following general formula (5) or the general formula (6),

$$MM^R D_{v-1} \quad (5)$$

$$M_w D_{v-1} D^R{}_{v-2} T^R{}_{v-3} \quad (6)$$

(in the formulae, M, $M^R$, D, $D^R$, and $T^R$ have the same meanings defined above; v-1 represents a number satisfying $0 \le v\text{-}1 \le 500$; v-2 and v-3 each represent 0 or 1; with the proviso that the sum of v-2 and v-3 is 1, and the both of v-1 and v-3 are not 1 or more at the same time; and "w" represents an integer of 2 to 3)).

Such a silicone compound shown by the average composition formula (1) has a very high affinity for various oil materials such as silicone oil, ester oil, and hydrocarbon oil; and has excellent emulsifying property, by which the emulsion shows very good stability; thereby being very efficient in cosmetic uses.

The silicone compound is preferably the one shown by the following structural formula (1-1),

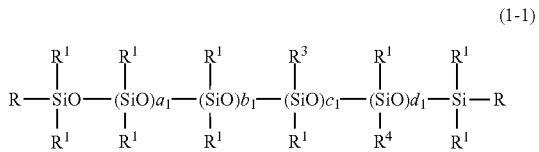

(In the formula, $R^1$, $R^2$, $R^3$, and $R^4$ have the same meanings as defined above; R represents the same or different group selected from $R^1$, $R^2$, $R^3$, and $R^4$; a1 represents a number in a range of 0 to 1000, b1 represents a number in a range of 0 to 200, c1 represents a number in a range of 0 to 200, d1 represents a number in a range of 0 to 100; with the proviso that at least one R is $R^2$ when b1=0, and at least one R is $R^3$ when c1=0.)

Such a silicone compound shown by the structural formula (1-1) is preferable in view of synthesis since the polymerization reaction thereof proceeds easily.

The silicone compound is preferably the one in which the "p" in the general formula (4) satisfies p=1.

The silicone compound with the "p" satisfies p=1 has little steric hindrance in the synthesis thereof, thereby being preferable in view of synthesis.

The present invention also provides a cosmetic comprising the foregoing silicone compound.

By blending the silicone compound to a cosmetic as an emulsifier, excellent temporal stability and a good use feeling can be obtained.

Advantageous Effects of Invention

The inventive silicone compound has excellent emulsifying property and emulsion stability to an oil material used for general cosmetics such as silicone oil, ester oil, and hydrocarbon oil for cosmetics, including a mixed oil material thereof; and can secure high stability with the passage of time. The cosmetic comprising the inventive silicone compound has a fresh and good use feeling as well as excellent storage stability.

DESCRIPTION OF EMBODIMENTS

The present inventors diligently study to achieve the foregoing objects and consequently found that the use of a silicone compound shown by the following average composition formula (1) and having a weight-average molecular weight in the range of 500 to 200,000 as an emulsifier gives very high affinity with various oil materials such as silicone oil and a mixed oil material thereof, excellent emulsifying property and very good stability of the emulsion therefrom, and is very efficient in cosmetic uses; thereby brought the present invention to completion.

Thus the present invention provides a silicone compound shown by the following average composition formula (1) and having a weight-average molecular weight in the range of 500 to 200,000,

$$R^1{}_a R^2{}_b R^3{}_c R^4{}_d SiO_{(4-a-b-c-d)/2} \quad (1)$$

(wherein "a", "b", "c", and "d" each represent a number satisfying $1.0 \le a \le 2.5$, $0.001 \le b \le 1.5$, $0.001 \le c \le 1.5$, and $0 \le d \le 1.0$;

$R^1$ represents the same or different organic group selected from an alkyl group having 1 to 30 carbon atoms, an aryl group, an aralkyl group, a fluorine-substituted alkyl group, and an organic group shown by the general formula (2) $-C_l H_{2l}-O-R^5$, (in the formula, $R^5$ represents a hydrogen atom, a hydrocarbon group having 4 to 30 carbon atoms, or an organic group shown by $R^9-(CO)-$; $R^9$ represents a hydrocarbon group having 1 to 30 carbon atoms; and "l" represents an integer satisfying $0 \le l \le 15$);

$R^2$ represents the same or different polyoxyalkylene group shown by the general formula (3) $-C_m H_{2m}-O-(C_2 H_4 O)_g (C_3 H_6 O)_h R^6$, (in the formula, $R^6$ represents a hydrogen atom, a hydrocarbon group having 1 to 30 carbon atoms, or an organic group shown by $R^9-(CO)-$; $R^9$ has the same meaning defined above; and "g" and "h" each represent an integer satisfying $2 \le g \le 200$, $0 \le h \le 200$, and g+h is 3 to 200; and "m" represents an integer satisfying $1 \le m \le 15$);

$R^3$ represents the same or different branched type monovalent organosiloxane group shown by the following general formula (4),

$$M_o M^R{}_p D_q D^R{}_r T_s T^R{}_t Q_u \quad (4)$$

(wherein $M=R^7{}_3 SiO_{0.5}$, $M^R=R^7{}_2 R^8 SiO_{0.5}$, $D=R^7{}_2 SiO$, $D^R=R^7 R^8 SiO$, $T=R^7 SiO_{1.5}$, $T^R=R^8 SiO_{1.5}$, and $Q=SiO_2$; $R^7$ represents the same or different organic group selected from an alkyl group having 1 to 30 carbon atoms, an aryl group, an aralkyl group, and a fluorine-substituted alkyl group; $R^8$ represents an organic group shown by $-C_n H_{2n}-$; "n" represents an integer satisfying $1 \le n \le 5$; "o" represents an integer of 1 or more; "q" and "s" each represent an integer of 0 or more; "p", "r", "t", and "u" each represent 0 or 1; with the proviso that "s", "t", and "u" are not equal to 0 at the same time, the sum of "p", "r", and "t" is 1, and when q=0, "o" is 2 or more and the sum of "s" and "u" is 1 or more);

$R^4$ represents the same or different monovalent organosiloxane group shown by the following general formula (5) or the general formula (6),

$$MM^R D_{v-1} \quad (5)$$

$$M_w D_{v-1} D^R{}_{V-2} T^R{}_{v-3} \quad (6)$$

(wherein M, $M^R$, D, $D^R$, and $T^R$ have the same meanings defined above; v-1 represents a number satisfying $0 \le v\text{-}1 \le 500$; v-2 and v-3 each represent 0 or 1; with the proviso that the sum of v-2 and v-3 is 1, and the both of v-1 and v-3 are not 1 or more at the same time; and "w" represents an integer of 2 to 3)).

In the foregoing formula (1), $R^1$ represents the same or different organic group selected from an alkyl group having 1 to 30 carbon atoms, an aryl group, an aralkyl group, a fluorine-substituted alkyl group, and an organic group shown by the general formula (2) —$C_lH_{2l}$—O—$R^5$.

Regarding $R^1$, illustrative examples of the alkyl group include a methyl group, an ethyl group, a propyl group, a butyl group, a pentyl group, a hexyl group, a heptyl group, an octyl group, a nonyl group, a decyl group, a cyclopentyl group, and a cyclohexyl group. Illustrative examples of the aryl group include a phenyl group and a tolyl group. Illustrative examples of the aralkyl group include a benzyl group and phenethyl group. Illustrative examples of the fluorine-substituted alkyl group include a trifluoropropyl group and a heptadecafluorodecyl group.

Alternatively, $R^1$ may be the same or different organic group shown by the general formula (2) —$C_lH_{2l}$—O—$R^5$ including an alkoxy group, an ester group, an alkenylether residue, and an alkenylester residue. Provided that $R^5$ in formula (2) represents a hydrogen atom, a hydrocarbon group having 4 to 30 carbon atoms, or an organic group shown by $R^9$—(CO)—; $R^9$ represents a hydrocarbon group having 1 to 30 carbon atoms; and "l" represents an integer satisfying $0 \leq l \leq 15$.

Illustrative examples of the hydrocarbon group having 4 to 30 carbon atoms of $R^5$ include a butyl group, a pentyl group, a hexyl group, a heptyl group, an octyl group, a nonyl group, a decyl group, a cyclopentyl group, a cyclohexyl group, a phenyl group, a tolyl group, a benzyl group, a phenethyl group. Illustrative examples of the hydrocarbon group having 1 to 30 carbon atoms of $R^9$ include a methyl group, an ethyl group, a propyl group, a butyl group, a pentyl group, a hexyl group, a heptyl group, an octyl group, a nonyl group, a decyl group, a cyclopentyl group, a cyclohexyl group, a phenyl group, a tolyl group, a benzyl group, a phenethyl group.

For example, when "l" is 0, a silanol (—OH) or an alkoxy group having 4 to 30 carbon atoms are exemplified, including examples from a lower alkoxy group such as a butoxy group to a higher alkoxy group such as an oleyloxy group and a stearoxy group. It can also be an ester group of acetic acid, lactic acid, butylic acid, oleic acid, stearic acid, or behenic acid.

When "l" is 1 or more, "l" is preferably 3, 5, or 11 in particular. In this case, $R^1$ includes a residue of allylether, pentenylether, and undecenylether, and the illustrative examples thereof include an allyl stearyl ether residue, propenyl behenyl ether residue, and undecenyl oleyl ether residue depending on the substituent of $R^5$.

Herein, "l" is 15 or less since the oily odor becomes strong when "l" is larger than 15. Further, "l" is preferably 3 to 5 also in view of resistance to hydrolysis.

In the present invention, $R^1$ in the formula (1) is preferably constituted of 50% or more of methyl group, more preferably 70% or more of methyl group on the basis of the total $R^1$, and can be constituted of 100% of methyl group.

In the foregoing formula (1), $R^2$ represents the same or different polyoxyalkylene group shown by the general formula (3) —$C_mH_{2m}$—O—$(C_2H_4O)_g(C_3H_6O)_hR^6$. $R^6$ in the formula (3) represents a hydrogen atom, a hydrocarbon group having 1 to 30 carbon atoms, or an organic group shown by $R^9$—(CO)—. Herein, "m" represents an integer of 1 to 15, preferably 3 to 5; "g" represents an integer of 2 to 200, preferably 5 to 100; "h" represents an integer of 0 to 200, preferably 0 to 100; and g+h is 3 to 200, preferably 5 to 100, and it is desirable that $g/h \leq 1$ in order to give sufficient hydrophilic nature to form water-in-oil emulsion.

Illustrative examples of the hydrocarbon group having 1 to 30 carbon atoms of $R^6$ includes the same sort of ones exemplified as specific examples of $R^9$.

Incidentally, when the polyoxyalkylene moiety in the formula (3) is composed of both ethyleneoxide units and propyleneoxide units, either a block copolymer or a random copolymer thereof can be included.

In the foregoing formula (1), $R^3$ represents the same or different branched type monovalent organosiloxane group shown by the following general formula (4), $$M_o M^R_p D_q D^R_r T_s T^R_t Q_u \quad (4)$$

(wherein $M=R^7_3SiO_{0.5}$, $M^R=R^7_2R^8SiO_{0.5}$, $D=R^7_2SiO$, $D^R=R^7R^8SiO$, $T=R^7SiO_{1.5}$, $T^R=R^8SiO_{1.5}$, and $Q=SiO_2$).

$R^7$ represents the same or different organic group selected from an alkyl group having 1 to 30 carbon atoms, an aryl group, an aralkyl group, and a fluorine-substituted alkyl group. Illustrative examples thereof include an alkyl group such as a methyl group, an ethyl group, a propyl group, a butyl group, a pentyl group, a hexyl group, a heptyl group, an octyl group, a nonyl group, a decyl group, a cyclopentyl group, and a cyclohexyl group; an aryl group such as a phenyl group and a tolyl group; an aralkyl group such as a benzyl group and a phenethyl group; and a fluorine-substituted alkyl group such as a trifluoropropyl group and a heptadecafluorodecyl group.

$R^7$ is preferably constituted of 50% or more of methyl group, more preferably 70% or more of methyl group on the basis of the total $R^7$, and can be constituted of 100% of methyl group.

$R^8$ represents an organic group shown by —$C_nH_{2n}$—; "n" represents an integer of 1 to 5, and preferably n=2.

Herein, "o" represents an integer of 1 or more, preferably 1 to 200, more preferably 1 to 100; "q" represents an integer of 0 or more, preferably 0 to 500, more preferably 1 to 200; "s" represents an integer of 0 or more, preferably 0 to 100, more preferably 1 to 50; "u" represents 0 or 1, preferably 1; "p", "r", and "t" each represent 0 or 1, and the sum of "p", "r", and "t" is 1, but it is preferred that p=1, which provides little steric hindrance, in view of synthesis; with the proviso that "s", "t", and "u" are not equal to 0 at the same time, and when q=0, "o" is 2 or more and the sum of "s" and "u" is 1 or more.

In the foregoing formula (1), $R^4$ represents the same or different monovalent organosiloxane group shown by the following general formula (5) or the general formula (6), $$MM^R D_{v-1} \quad (5)$$

$$M_w D_{v-1} D^R_{v-2} T^R_{v-3} \quad (6)$$

Wherein M, $M^R$, D, $D^R$, and $T^R$ have the same meanings defined above; v-1 represents a number of 0 to 500, preferably 3 to 50. When v-1 is larger than 500, it can cause lowering of the reactivity in the synthesis thereof. Each of v-2 and v-3 represents a number of 0 or 1, with the proviso that the sum of v-2 and v-3 is 1, and the both of v-1 and v-3 are not 1 or more at the same time; and "w" represents an integer of 2 to 3.

Herein, "a" represents a number of 1.0 to 2.5, preferably 1.2 to 2.3. When "a" is smaller than 1.0, the compatibility with an oil material becomes worse, and stable emulsion is hard to obtain. When "a" is larger than 2.5, the hydrophilicity becomes poor, and stable emulsion is hard to obtain either. Next, "b" represents a number of 0.001 to 1.5, preferably 0.05 to 1.0. When "b" is smaller than 0.01, the hydrophilicity becomes poor, and stable emulsion is hard to obtain. When "b" is larger than 1.5, the hydrophilicity becomes too high, and stable emulsion is hard to obtain. Moreover, "c" represents a number of 0.001 to 1.5, preferably 0.05 to 1.0. When "c" is smaller than 0.001, the compatibility with silicone oil becomes worse, and stable emulsion is hard to obtain. When "c" is larger than 1.5, the hydrophilicity becomes poor, and stable emulsion is hard to obtain either. In addition, "d" represents a number of 0 to 1.0, preferably 0 to 0.5. When "d" is larger than 1.0, the hydrophilicity becomes poor, and stable emulsion is hard to obtain.

As an emulsifier, the silicone compound shown by the average composition formula (1) has a weight-average molecular weight in the range of 500 to 200,000, preferably in the range of 1,000 to 100,000. When the molecular weight is less than 500, stable emulsion is hard to obtain. When the molecular weight is larger than 200,000, the handling property becomes worse, and a good use feeling is hard to obtain. Herein the weight-average molecular weight can be determined by a gel permeation chromatography (GPC) analysis in terms of polystyrene (which will be also applied in the following).

The silicone compound shown by the formula (1) is preferably the one shown by the following structural formula (1-1) since it can be synthesized easily,

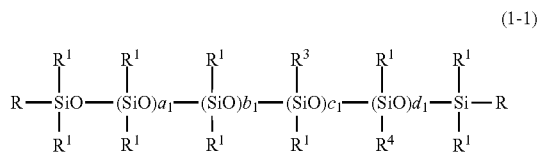

(1-1)

(wherein $R^1$, $R^2$, $R^3$, and $R^4$ have the same meanings as defined above; R represents the same or different group selected from $R^1$, $R^2$, $R^3$, and $R^4$; a1 represents a number in a range of 0 to 1000, b1 represents a number in a range of 0 to 200, c1 represents a number in a range of 0 to 200, d1 represents a number in a range of 0 to 100; with the proviso that at least one R is $R^2$ when b1=0, and at least one R is $R^3$ when c1=0).

The inventive silicone compound shown by the formula (1) can be synthesized easily by addition reaction of organohydrogenpolysiloxane, a polyoxyalkylene compound having a $C_mH_{(2m-1)}-$ group, a silicone compound having a $C_nH_{(2n-1)}-$ group, and further an alkene-terminated compound in case of need, in the presence of a platinum catalyst or a rhodium catalyst. Herein, "m" and "n" have the same meanings as defined above.

The organohydrogenpolysiloxane can be any of linear, branched, cyclic type. However, in order to smoothly performs the polymerization reaction, it is preferable to be linear, mainly a linear type as shown by the following formula (1-2),

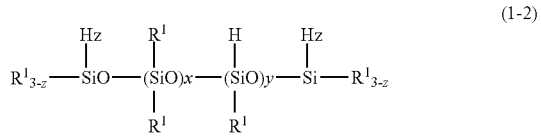

(1-2)

In the formula (1-2), $R^1$ represents the foregoing group, and "x" represents a number satisfying 0≤x≤1000, preferably 0≤x≤300, more preferably 0≤x≤100. When "x" is 1000 or less, there arises no risk to lower the reactivity and to deteriorate the usability. Moreover, "y" represents a number satisfying 0≤y≤300, preferably 1≤y≤100, more preferably 25≤y≤50. When "y" is 300 or less, there arises no risk to cause such a high hydrophilicity that stable emulsion is hard to obtain, and the reaction is easy to perfectly finish. Furthermore, "z" represents a number of 0 to 2, preferably 0 to 1.

Illustrative examples of the polyoxyalkylene compound having a $C_mH_{(2m-1)}-$ group include $C_mH_{(2m-1)}-O-(C_2H_4O)_q(C_3H_6O)_hR^6$, wherein $R^6$, "g", "h", and "m" have the same meanings defined above.

As the silicone compound having a $C_nH_{(2n-1)}-$ group, it is possible to use a silicone compound shown by the following general formula (7), and a silicone compound shown by the following general formula (8) or the general formula (9) in case of need.

$$M_oM^{R'}_pD_qD^{R'}_rT_sT^{R'}_tQ_u \quad (7)$$

(wherein $M=R^7{}_3SiO_{0.5}$, $M^{R'}=R^7{}_2R^{15}SiO_{0.5}$, $D=R^7{}_2SiO$, $D^{R'}=R^7R^{15}SiO$, $T=R^7SiO_{1.5}$, $T^{R'}=R^{15}SiO_{1.5}$, and $Q=SiO_2$; $R^{15}$ represents an organic group shown by $C_nH_{(2n-1)}-$; $R^7$, "n", "o", "p", "q", "r", "s", "t", and "u" have the same meanings defined above. Incidentally, when p=1, the steric hindrance is small, and high reactivity can be realized thereby).

Such a silicone compound shown by the general formula (7) has one organic group shown by $C_nH_{(2n-1)}-$, and has a branched structure ("s", "t", and "u" are not equal to 0 at the same time; the sum of "p", "r", and "t" is 1; and when q=0, "o" is 2 or more and the sum of "s" and "u" is 1 or more), which has high functionality. Such compounds have very good reactivity and are suitable for a raw material of the inventive silicone compound.

$$MM^{R'}D_{v-1} \quad (8)$$

$$M_vD_{v-1}D^{R'}_{v-2}T^{R'}_{v-3} \quad (9)$$

(wherein $M=R^7{}_3SiO_{0.5}$, $M^{R'}=R^7{}_2R^{15}SiO_{0.5}$, $D=R^7{}_2SiO$, $D^{R'}=R^7R^{15}SiO$, $T=R^7SiO_{1.5}$, $T^{R'}=R^{15}SiO_{1.5}$, and $Q=SiO_2$; $R^{15}$ represents an organic group shown by $C_nH_{(2n-1)}-$; $R^7$, v-1, v-2, and v-3 have the same meanings defined above. Incidentally, when v-1 is larger than 500, it can cause lowering of the reactivity with organohydrogenpolysiloxane, etc.)

The silicone compound obtained by adding linear organosiloxane or branched low-molecular weight organosiloxane shown by the general formula (8) or the general formula (9) gives a more fresh and light feeling when it is contained in a cosmetic.

As the alkene terminated compound, an alkene terminated compound having 6 to 30 carbon atoms is preferable, and illustrative example thereof include 1-dodecene. A silicone compound obtained by adding a long chain-alkene terminated compound such as 1-dodecene has higher affinity with an oil material used for general cosmetics such as silicone oil, ester oil, and hydrocarbon oil; and accordingly it is possible to obtain a silicone compound having excellent emulsifying property.

The blending ratio between the organohydrogenpolysiloxane, and the sum of the polyoxyalkylene compound having a $C_mH_{(2-x)}-$ group, the silicone compound having a $C_nH_{(2n-1)}-$ group, and the alkene terminated compound is preferably 0.5 to 2.0, more preferably 0.8 to 1.2 in a molar ratio of the terminal unsaturated group on the basis of 1 mole of the SiH group.

It is desirable to perform the foregoing addition reaction in the presence of a platinum catalyst or a rhodium catalyst.

Specifically, chloroplatinic acid, alcohol modified-chloroplatinic acid, chloroplatinic acid-vinylsiloxane complex, etc. are favorably used. The content of the catalyst can be a catalytic amount, but preferably 0.01 to 50 ppm, more preferably 0.1 to 20 ppm in terms of an amount of platinum or rhodium relative to the total mass of the raw materials to be used. When the amount of the catalyst is in the foregoing range, an addition reaction proceeds without lowering the reaction speed, and is favorable from the economical viewpoint.

The foregoing addition reaction can be performed in an organic solvent in case of need. Illustrative examples of the organic solvent include aliphatic alcohol such as methanol, ethanol, 2-propanol, and butanol; aromatic hydrocarbon such as toluene and xylene; aliphatic or alicyclic hydrocarbon such as n-pentane, n-hexane, and cyclohexane; and halogenated hydrocarbon such as dichloromethane, chloroform, and carbon tetrachloride. Particularly, ethanol and 2-propanol (isopropyl alcohol) are favorable for cosmetic uses. The addition reaction condition is not particularly limited, but it is favorable to react under reflux for 1 to 10 hours. The amount of the solvent is not particularly limited, and can be adjusted appropriately.

It is also possible to perform hydrolysis of the residual SiH group by using alkaline material in case of need. The reaction can be performed only with water, but is preferably performed by adding alkaline material in order to control the reaction constantly. The amount of the alkaline material to be added in hydrolysis of the residue SiH group is preferably 0.0001 to 10 parts by mass, more preferably 0.001 to 10 parts by mass relative to 100 parts by mass of the organohydrogenpolysiloxane to be used. When the amount is 0.0001 parts by mass or more, sufficient hydrolysis effect can be obtained. When the amount is 10 parts by mass or less, an unfavorable reaction such as scission of a siloxane chain can be avoided. The alkaline material can be added as it is, but is preferably added in a form of 1 to 50% by mass of aqueous solution in view of contact efficient with organohydrogenpolysiloxane.

As a treating condition after adding the alkaline material, it is preferable to heat to 10 to 80° C., particularly 10 to 50° C. It is also possible to add an acidic material to perform neutralization reaction after finishing the hydrolysis reaction. The acidic material may be added as it is or in a form of 1 to 50% by mass of aqueous solution. The amount can be adjusted in such a way that the pH after the neutralization is 5 to 8, and an equivalent ratio of functional groups of the alkaline material and the acidic material is preferably 1/0.1 to 0.1/1, more preferably 1/0.3 to 0.3/1.

Furthermore, purification treatment by use of acidic material may be applied if needed. The treatment can be performed with water alone, but it is preferable to add acidic material in order to control the reaction constant. The amount of the acidic material is preferably 0.0000001 to 10 parts by mass, more preferably 0.000001 to 1 part by mass relative to 100 parts by mass of the silicone compound shown by the average composition formula (1). When the amount is 0.0000001 parts by mass or more, deodorizing effect can be sufficiently obtained. The amount of 10 parts by mass or less is preferable since it does not cause a risk to precipitate many neutralized salt in the treated composition. The acidic material may be added as it is, but preferably added in a form of 1 to 50% by mass of aqueous solution in view of contact efficient with a liquid to be treated.

As a treating condition after an addition of the acidic material, heating is not essential, but it is preferable to perform heating at a temperature of 20 to 150° C., particularly 50 to 100° C. In case of performing the neutralization reaction by using alkaline material, the alkaline material may be added as it is, but preferably added in a form of 1 to 50% by mass of aqueous solution. The amount can be adjusted in such a way that the pH after the neutralization is 5 to 8, and an equivalent ratio of functional groups of the acidic material and the alkaline material is preferably 1/0.1 to 0.1/1, more preferably 1/0.3 to 0.3/1. The treatment condition after an addition of the alkaline neutralizing agent is preferably 20 to 150° C., particularly 20 to 80° C.

Illustrative examples of the alkaline material include sodium carbonate, sodium hydrogencarbonate, sodium hydroxide, potassium hydroxide, disodium hydrogenphosphate, and sodium acetate; and particularly, sodium carbonate, sodium hydrogencarbonate, and sodium hydroxide are preferable. As the acidic material, inorganic acid, organic acid, and salt thereof can be used. Illustrative examples of the inorganic acid include hydrochloric acid, sulfuric acid, nitric acid, carbonic acid, and phosphoric acid. Illustrative examples of the organic acid include carboxylic acid such as formic acid, acetic acid, and trifluoroacetic acid; sulfonic acid, sulfinic acid, phenolic acid, primary and secondary nitro compound. In view of treatment efficiency, the use of strong acid such as hydrochloric acid or trifluoroacetic acid is preferable. However, they are preferably selected from combinations by which the neutralization reaction produces salt having buffer effect on the pH. This makes it possible to lower the odor and to obtain an effect of stabilizing the pH of a composition. The specific procedure for this treatment follows a method described in PATENT LITERATURE 7.

The branched type organopolysiloxane shown by the general formula (7) having a $C_nH_{(2n-1)}$— group, which forms a branched type monovalent organosiloxane group shown by the general formula (4) after the addition reaction, can be obtained by reacting an organosiloxane having only one silanol group in the molecule with an organic chlorosilane compound in the presence of a base. Specifically, it can be obtained by [Step 1] and [Step 2], or repeating [Step 1] and [Step 2], which are described below.

[Step 1] is a step to obtain an organosiloxane having only one silanol group in the molecule by reacting an organohydrogensiloxane shown by the following general formula (10) with water in the presence of a catalyst:

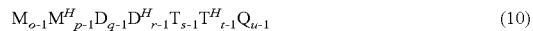

$$M_{o-1}M^H_{p-1}D_{q-1}D^H_{r-1}T_{s-1}T^H_{t-1}Q_{u-1} \qquad (10)$$

wherein $M=R^7_3SiO_{0.5}$, $M^H=R^7_2HSiO_{0.5}$, $D=R^7_2SiO$, $D^H=HR^7SiO$, $T=R^7SiO_{1.5}$, $T^H=HSiO_{1.5}$, and $Q=SiO_2$; $R^7$ has the same meaning as defined above; o-1 represents an integer of 1 or more; q-1 and s-1 each represent an integer of 0 or more; p-1, r-1, t-1, and u-1 each represent 0 or 1; with the proviso that s-1, t-1, and u-1 are not equal to 0 at the same time, the sum of p-1, r-1, and t-1 is 1, and when q-1=0, o-1 is 2 or more and the sum of s-1 and u-1 is 1 or more.

Illustrative examples of the production method of organohydrogensiloxane shown by the general formula (10), which is already known art, include hydrolysis condensation and living polymerization of an organosilicon compound having a SiH group and an organosilicon compound having an alkyl group, and can involve purification treatment such as distillation if needed. It is also possible to purchase a commercial product.

As the catalyst to be used, a transition metal catalyst and a Lewis acid catalyst are mentioned. Illustrative examples of the transition metal catalyst include a ruthenium catalyst, a rhodium catalyst, a palladium catalyst, an iridium catalyst, a platinum catalyst, and a gold catalyst, and the palladium catalyst is particularly preferable. Illustrative examples of the Lewis acid catalyst include aluminum chloride, aluminum sulfate, stannic chloride, stannic chloride sulfate, ferric chloride, boron trifluoride, and pentafluorophenylborane, and pentafluorophenylborane is particularly preferable.

In [Step 1], solvent may be used in case of need. The solvent is not particularly limited as long as it is non-reactive to the organohydrogensiloxane shown by the general formula (10) of raw material and the catalyst. Illustrative example thereof include aliphatic hydrocarbon type solvent such as pentane, hexane, heptane, and decane; aromatic hydrocarbon type solvent such as benzene, toluene, and xylene; and ether type solvent such as diethyl ether, tetrahydrofuran, and 1,4-dioxane. The amount of the solvent is not particularly limited, and can be adjusted appropriately.

When the organosiloxane having only one silanol group in the molecule is produced in [Step 1], the blend ratio of organohydrogensiloxane of the general formula (10) and a catalyst is not particularly limited. In view of its reactivity and productivity, however, it is preferable to react the catalyst in a range of 0.000001 to 0.1 mole, particularly 0.000001 to 0.01 mole on the basis of 1 mole of organohydrogensiloxane of the general formula (10). When the amount is 0.000001 mole or more, the reaction rate is not lowered, and the reaction time is reduced. The amount of 0.1 mole or less is preferable since it does not cause a risk of lowering the yield due to polymerization through redistribution reaction of the organosiloxane having only one silanol group in the molecule, which is a reaction product.

In producing the organosiloxane having only one silanol group in the molecule, the blend ratio of organohydrogensiloxane of the general formula (10) and water is not particularly limited. In view of its reactivity and productivity, however, it is preferable to react water in a range of 1 to 5 mole, particularly 1.05 to 3.0 mole on the basis of 1 mole of organohydrogensiloxane of the general formula (10). When the amount is 1 mole or more, the reaction proceeds completely to give a sufficient yield. When the amount is 5 mole or less, a sufficient pot yield can be obtained while enhancing the yield.

In [Step 1], the reaction temperature is preferably in a range of 1 to 70° C., particularly 5 to 40° C. As the reaction time, it is preferable to perform the reaction for 30 minutes to 10 hours, particularly 1 to 8 hours, though it depends on the degree of reaction progress. It is also possible to perform purification treatment such as distillation when it is needed. The purification can be carried out by a conventional method under normal pressure or reduced pressure.

[Step 2] is a step to react the organosiloxane having only one silanol group in its molecule obtained in [Step 1] with an organic chlorosilane compound in the presence of a base.

The base of a raw material required in [Step 2] is not particularly limited. Illustrative examples thereof include sodium carbonate, and amine type base such as pyridine, triethylamine, ammonia, methylamine, ethylamine, dimethylamine, N-hexylamine, N-ethyldiisopropylamine, imidazole, N-methylimidazole.

The organic chlorosilane compound of a raw material is not particularly limited. If the obtained compound is used as a silicone compound shown by the general formula (7), the organic chlorosilane compound having a $C_nH_{(2n-1)}$— group is preferable, and particularly, dimethylvinylchlorosilane is on the market and easily available. When the obtained compound is used as a compound of the general formula (10) in [Step 1] to obtain a polymer having highly branched structure, dimethylchlorosilane, methyldichlorosilane, and trichlorosilane are on the market and easily available.

In [Step 2], solvent may be used in case of need. The solvent is not particularly limited as long as it is non-reactive to raw materials such as the organohydrogensiloxane shown by the general formula (10), a base, and an organic chlorosilane compound. Illustrative example thereof include aliphatic hydrocarbon type solvent such as pentane, hexane, heptane, and decane; aromatic hydrocarbon type solvent such as benzene, toluene, and xylene; and ether type solvent such as diethyl ether, tetrahydrofuran, and 1,4-dioxane. The amount of the solvent is not particularly limited, and can be adjusted appropriately.

In producing the branched type organopolysiloxane having a $C_nH_{(2n-1)}$— group shown by the general formula (7), the blend ratio of organosiloxane having only one silanol group in the molecule obtained in [Step 1] and an organic chlorosilane compound is not particularly limited. In view of its reactivity and productivity, however, it is preferable to react the Si—Cl group in the organic chlorosilane compound in a range of 0.01 to 2.0 mole, particularly 0.4 to 1.2 mole on the basis of 1 mole of the organosiloxane obtained in [Step 1]. When the amount is 0.01 mole or more, the yield of the branched type monofunctional organosiloxane compound is sufficient. When the amount is 2.0 mole or less, a sufficient pot yield can be obtained while enhancing the yield.

In [Step 2], the blend ratio of an organic chlorosilane compound and a base is not particularly limited. In view of its reactivity and productivity, however, it is preferable to react the base in a range of 0.1 to 6.0 mole, particularly 0.4 to 3.0 mole on the basis of 1 mole of the Si—Cl group in the organic chlorosilane compound. When the amount is 0.1 mole or more, the reaction rate is not lowered, and the reaction time is reduced. The amount of 6.0 mole or less makes it easy to isolate a branched type monofunctional organosiloxane compound, which is a reaction product, and gives a sufficient yield.

The reaction temperature of [Step 2] is preferably in a range of 1 to 80° C., particularly 5 to 40° C. The reaction time is preferably in a range of 30 minutes to 20 hours, particularly 1 to 10 hours.

In [Step 2], when amine such as ammonia is used as a base, it is also possible to carry out the reaction via organic silazane by reacting organic chlorosilane previously. In this method, by-product of salt can be suppressed. It is preferable to perform this reaction at a temperature in a range of 1 to 80° C., particularly 5 to 50° C. The reaction time is preferably in a range of 30 minutes to 20 hours, particularly 1 to 10 hours.

In this production method, it is also possible to perform purification treatment such as distillation in case of need. The purification can be carried out by a conventional method under normal pressure or reduced pressure.

The inventive silicone compound can be used for various uses. In particular, it is suitable for raw materials of every cosmetic externally used for skin or hair. In this case, the blending amount of the silicone compound shown by the average composition formula (1) is preferably in a range of 0.1 to 50% by mass relative to the total amount of the cosmetic in general, though it varies depending on the types and dosage form of the cosmetics.

The inventive cosmetic preferably contains silicone oil in addition to the silicone compound shown by the average composition formula (1). Illustrative examples of the preferable silicone oil include dimethylpolysiloxane, methylphenylpolysiloxane, methyltrimethicone, phenyltrimethicone, decamethylcyclopentasiloxane, dodecamethylcyclohexasiloxane, octamethyltrisiloxane, decamethyltetrasiloxane, dodecamethylpentasiloxane, heptamethylethyltrisiloxane, caprylylmethicone, and tetrakistrimethylsiloxysilane. Since the silicone compound shown by the average composition formula (1) has an excellent emulsifying property to silicone oil, the inventive cosmetic improves the stability of an emulsion cosmetic by containing silicone oil. Furthermore, a cosmetic with no stickiness can be obtained. These silicone oil can be used singly, or as a mixture of two or more of them. The blending amount of the silicone oil is preferably 2 to 40% by mass, particularly 5 to 20% by mass relative to the total amount of the cosmetic. The amount in a range of 2 to 40% by mass is preferable since it does not deteriorate the emulsion stability.

Preferably, the inventive cosmetic further contains non-emulsifiable silicone elastomer. The non-emulsifiable silicone elastomer is preferably a one which is swollen with low-viscosity silicone having a kinematic viscosity of 0.65 to 10.0 mm$^2$/s (at 25° C.) measured with an Ostwald viscometer to contain the low-viscosity silicone more than its own weight. This non-emulsifiable silicone elastomer preferably has a crosslinked structure formed through the reaction between a crosslinking agent having two or more of vinyl type reaction moieties in the molecule and hydrogen atoms directly bonded to a silicon atom(s). Furthermore, this non-emulsifiable silicone elastomer preferably has at least one moiety selected from the group consisting of an alkyl moiety, an alkenyl moiety, an aryl moiety, and a fluoroalkyl moiety. In case of using the non-emulsifiable silicone elastomer, the content is preferably 0.1 to 30% by mass, particularly 1 to 10% by mass relative to the total amount of the cosmetic.

Illustrative examples of the non-emulsifiable silicone elastomer include a dimethicone/vinyldimethicone crosspolymer manufactured by Shin-Etsu Chemical Co., Ltd. (KSG-15, KSG-16), a dimethicone/phenylvinyldimethicone crosspolymer manufactured by Shin-Etsu Chemical Co., Ltd. (KSG-18, etc.), a vinyldimethicone/lauryldimethicone crosspolymer manufactured by Shin-Etsu Chemical Co., Ltd. (KSG-41, etc.), and a dimethicone crosspolymer designated to INCI. As the non-emulsifiable silicone elastomer, it is also possible to use a dimethicone/vinyldimethicone crosspolymer manufactured by Shin-Etsu Chemical Co., Ltd. (KMP-400, etc.) or a vinyldimethicone/methicone silsesquioxane crosspolymer manufactured by Shin-Etsu Chemical Co., Ltd. (KMP-100, etc.).

The blend of the non-emulsifiable silicone elastomer further enhances the emulsion stability, provides a cosmetic with excellent cosmetic durability and no stickiness, and gives a moisture feeling.

The inventive cosmetic can contain alcohols; solid, semi-solid, or liquid oil material (other than the silicone oil exemplified above); water, etc., which are used for conventional cosmetics. These are illustrated in the following, but the present invention is not limited thereto.

Illustrative example of the alcohols usable in the present invention includes ethanol, propanol, ethylene glycol, ethylene glycol monoalkyl ether, diethylene glycol monoethyl ether, polyethylene glycol, propylene glycol, dipropylene glycol, 1,3-butylene glycol, glycerin, diglycerin, polyglycerin, pentaerythritol, sucrose, lactose, xylitol, sorbitol, mannitol, maltitol, carrageenan, agar, guar gum, dextrin, tragacanth gum, locust bean gum, polyvinyl alcohol, a polyoxyethylene-type polymer, a polyoxyethylene polyoxypropylene copolymer type polymer, hyaluronic acid, chondroitin sulfate, and chitin chitosan; these may be used singly, or as a mixture of two or more of them in case of need. The content of these alcohols in the cosmetic is in the range of 0.1 to 90.0% by mass, or preferably 0.5 to 50.0% by mass. If the content thereof is 0.1% by mass or more, sufficient moist property, antibacterial property, and antimold property may be obtained; while, if the content thereof is 90.0% by mass or less, effect of the inventive cosmetic can be fully expressed.

Illustrative example of higher alcohols includes lauryl alcohol, myristyl alcohol, palmityl alcohol, stearyl alcohol, behenyl alcohol, hexadecyl alcohol, oleyl alcohol, isostearyl alcohol, hexyl dodecanol, octyl dodecanol, cetostearyl alcohol, 2-decyl tetradecynol, cholesterol, phytosterol, POE cholesterol ether, monostearyl glycerin ether (batyl alcohol), and monooleyl glycerine ether (selachyl alcohol).

As to the oils usable in the present invention other than silicone oil, following substances can be exemplified. Meanwhile, POE means polyoxyethylene.

Illustrative example of natural vegetable and animal fatty oils and semi-synthetic oils includes an avocado oil, a linseed oil, an almond oil, a Chinese wax (an insects wax), a perilla oil, an olive oil, a cocoa butter, a kapok wax, a kaya oil, a carnauba wax, a liver oil, a candelilla wax, a beef tallow, a neats-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a shea butter, a Chinese tung oil, a cinnamon oil, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse fat, a palm oil, a palm kernel oil, a castor oil, a cured castor oil, a methyl ester of castor oil fatty acid, a sunflower oil, a grape seed oil, a bayberry wax, a jojoba oil, a macademia nut oil, a bees wax, a mink oil, a cotton seed oil, a cotton wax, a Japan wax, a Japan wax kernel oil, a montan wax, a coconut oil, a cured coconut oil, a tri-coconut fatty acid glyceride, a mutton tallow, a peanut oil, lanolin, liquid lanolin, reduced lanolin, lanolin alcohol, hard lanolin, lanolin acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil.

Illustrative example of hydrocarbon oils includes an ozocerite, squalane, squalene, a ceresin, a paraffin, a paraffin wax, isodecane, isododecane, isohexadecane, a liquid paraffin, a pristane, polyisobutylene, a microcrystalline wax, and vaseline. Illustrative example of higher fatty acids includes lauric acid, myristic acid, palmitic acid, stearic acid, behenic acid, undecylenic acid, oleic acid, linoleic acid, linolenic acid, arachidonic acid, eicosapentaenoic acid, docosahexaenoic acid, isostearic acid, and 12-hydroxystearic acid.

Illustrative example of the ester oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, neopentyl glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isononyl isononanate, triisohexanoin, isopropyl myristate, 2-octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, diisostearyl malate, dextrin palmitate ester, dextrin stearate ester, dextrin 2-ethylhexanoate palmitate ester, sucrose palmitate ester, sucrose stearate ester, monobenzylidene sorbitol, and dibenzylidene sorbitol.

Illustrative example of glyceride oils includes acetoglyceryl, glyceryl diisooctanoate, glyceryl triisostearate, glyceryl triisopalmitate, glyceryl tri-2-ethylhexanoate, glyceryl monostearate, glyceryl di-2-heptylundecanoate, and glyceryl trimyristate.

These oil materials other than silicone oils may be used singly, or as a mixture of two or more of them in case of need. The inventive cosmetic can contain the foregoing oil material with the amount thereof being 0 to 90% by mass, particularly 1 to 90% by mass relative to the total amount of the cosmetic.

If the inventive cosmetic contains water as its ingredient, preferable amount of water therein is 1 to 99% by mass.

The inventive cosmetic is excellent by containing those ingredients described above, but may further contain, in addition to the above, following ingredients i), ii), and iii), if necessary.

i) Powders and/or Colorants Shown Below

Illustrative example of the inorganic powder includes a powder of titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, silicic acid, silicic acid anhydride, aluminum silicate, magnesium silicate, aluminum magnesium silicate, calcium silicate, barium silicate, strontium silicate, a metal tungstate salt, hydroxy apatite, vermiculite, higilite, bentonite, montomorillonite, hectorite, zeolite, ceramic powder, dibasic calcium phosphate, alumina, aluminum hydroxide, boron nitride, and silica.

Illustrative example of the organic powder includes polyamide powder, polyester powder, polyethylene powder, polypropylene powder, polystyrene powder, polyurethane powder, bezoguanamine powder, polymethyl benzoguanamine powder, tetrafluoroethylene powder, polymethyl methacrylate powder, cellulose powder, silk powder, nylon powder such as 12 nylon and 6 nylon, and other powders of a styrene-acrylic acid copolymer, a divinyl benzene-styrene copolymer, a vinyl resin, an urea resin, a phenolic resin, a fluorine resin, a silicone resin, an acryl resin, a melamine resin, an epoxy resin, a polycarbonate resin, starch, lauroyl lysine, and fine crystalline fiber powder.

Illustrative example of the surfactant metal salt powder (metal soap) includes zinc stearate, aluminum stearate, calcium stearate, magnesium stearate, zinc myristate, magnesium myristate, zinc cetylphosphate, calcium cetylphosphate, and sodium cetylphosphate zinc.

Illustrative example of the color pigment includes an inorganic red pigment such as iron oxide, iron hydroxide, and iron titanate; an inorganic brown pigment such as γ-iron oxide; an inorganic yellow pigment such as yellow iron oxide and loess; an inorganic black pigment such as black iron oxide and carbon black; an inorganic purple pigment such as manganese violet and cobalt violet; an inorganic green pigment such as chromium hydroxide, chromium oxide, cobalt oxide, and cobalt titanate; an inorganic blue pigment such as Prussian blue and ultramarine; a laked tar dye; a laked natural dye; and a composite powder obtained by hybridization of these powders.

Illustrative example of the pearl pigment includes a mica coated with titanium oxide, oxychloro bismuth, oxychloro bismuth coated with titanium oxide, talc coated with titanium oxide, argentine, and color mica coated with titanium oxide; and illustrative example of the metal powder pigment includes aluminum powder, copper powder, and stainless powder.

Illustrative example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and illustrative example of the natural dye includes carminic acid, laccaic acid, carthamin, brazilin, and crocin.

These powders may be used independent of their forms (spherical, needle-like, plate-like, and so on), their particle diameters (fumed, microparticle, pigment-class, and so on), and their particle structures (porous, non-porous, and so on), as far as they are used in a usual cosmetic. Further, these powders may form a composite by hybridizing with each other, or may be treated their surfaces with an oil, a silicone which is not expressed by the general formula (1), or a fluorinated compound.

In case of using the exemplified powders and/or colorants, each content is preferably 0 to 99% by mass, in particular 0.1 to 99% by mass, relative to the total amount of the cosmetic.

ii) Surfactants Shown Below

Illustrative example of the anionic surfactant includes a saturated or an unsaturated aliphatic acid soap such as sodium stearate and triethanolamine oleate, an alkyl ether carboxylic acid and a salt thereof, a carboxylate salt of a condensation product between an amino acid and a fatty acid or the like, an amide ether carboxylate salt, an α-sulfofatty acid ester salt, an α-acylsulfonate salt, an alkyl sulfonate salt, an alkene sulfonate salt, a sulfonate salt of a fatty acid ester, a sulfonate salt of a fatty acid amide, an alkyl sulfonate salt and a sulfonate salt of its formalin condensate, an alkyl sulfate ester salt, a sulfate ester salt of a secondary higher alcohol, a sulfate ester salt of an alkyl and an allyl ether, a sulfate ester salt of a fatty acid ester, a sulfate ester salt of a fatty acid alkylolamide, a sulfate ester salt of a Turkey red oil and so on, an alkyl phosphate salt, an alkenyl phosphate salt, an ether phosphate salt, an alkyl ally ether phosphate salt, an alkylamide phosphate salt, and an N-acylamino acid.

Illustrative example of the cationic surfactant includes an alkylamine salt, a salt of an amine such as polyamine and an aminoalcohol fatty acid derivative, an alkyl quaternary ammonium salt, an aromatic quaternary ammonium salt, a pyridium salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethyelene sorbitol fatty acid ester, a polyoxyethylene glycerin fatty acid ester, a polyoxyethylene propylene glycol fatty acid ester, a polyoxyethylene castor oil, a polyoxyethylene hydrogenated castor oil, a polyoxyethylene phytostanol ether, a polyoxyethylene phytosterol ether, a polyoxyethylene cholestanol ether, a polyoxyethylene cholesteryl ether, a polyoxyalkylene-modified organopolysiloxane, an organopolysiloxane co-modified with a polyoxyalkylene and an alkyl, an organopolysiloxane co-modified with a polyoxyalkylene and a fluoroalkyl, a polyoxyalkylene-organopolysiloxane block copolymer, an alkanol amide, a sugar ether, and a sugar amide. Illustrative example of the amphoteric surfactant includes a betaine, an aminocarboxylate salt, and an imidazoline derivative.

In case of using the exemplified surfactant, the content is preferably 0.1 to 20% by mass, in particular 0.2 to 10% by mass, relative to the total amount of the cosmetic.

iii) Silicone Resin Such as a Graft or a Block Acryl/Silicone Copolymer and a Silicone Net-Work Compound In accordance with its purpose, the inventive cosmetic can contain at least one silicone resin selected from a graft or a block acryl/silicone copolymer, a silicone net-work compound, etc. In the present invention, an acryl silicone resin is especially preferable as this silicone resin. Further, it is preferable that this silicone resin be an acryl silicone resin which contains in its molecule at least one moiety selected from the group consisting of a pyrrolidone moiety, a long-chain alkyl moiety, a polyoxyalkylene moiety, and a fluoroalkyl moiety. In addition, it is preferable that this silicone resin be a net-work silicone compound. When a silicone resin such as the graft or block acryl/silicone copolymer and the net-work silicone compound is used, the content is preferably 0.1 to 20% by mass, in particular 1 to 10% by mass, relative to the total amount of the cosmetic.

In addition to the foregoing ingredients, the inventive cosmetic can contain substances which are used in a usual cosmetic such as a water-soluble polymer, a film-forming material, an oil-soluble gelation agent, an organic-modified clay mineral, a resin, a UV-absorber, a moisturizer, an antibacterial preservative, an antibacterial agent, a perfume (fragrance), salts, an antioxidant, a pH controller, a chelating agent, an algefacient, an anti-inflammatory agent, a skin care ingredient, vitamins, amino acids, nucleic acid, a hormone, and a clathrate compound.

Specific preferable application of the inventive cosmetic includes a skin care product, a make-up product, a UV-cut product, an antiperspirant, and a hair care product. The form of the product is not particularly limited, and can be used in a form of liquid, milky emulsion, cream, solids, paste, gel, powder, multilayer, mousse, and spray.

EXAMPLES

Hereinafter, the present invention will be explained more specifically by showing Examples, but the present invention is not limited thereto. Incidentally, in Step 1, disappearance of Si—H and formation of Si—OH were confirmed by using a Fourier transform infrared spectrophotometer (FT-IR). $^1$H-NMR analyses were performed with AVANCE-III (manufactured by Bruker BioSpin K.K.) by using deuterated chloroform as a measuring solvent.

In the following Examples, the purities of reaction products were confirmed with a gas chromatograph equipped with a thermal conductivity detector under the following conditions.
Conditions for Measuring Gas Chromatography (GC)
Gas chromatograph: manufactured by Agilent Technologies Japan, Ltd.
Detector: FID (Flame Ionization Detector), temperature: 300° C.
Capillary column: J&W HP-5MS (0.25 mm×30 m×0.25 μm)
Temperature rising program: 50° C. (2 minutes)→10° C./minute→250° C. (holding)
Injection temperature: 250° C.
Carrier gas: helium (1.0 ml/min)
Sprit ratio: 50:1
Injection amount: 1 μl (Synthesis Example 1) Synthesis of Branched Type Organopolysiloxane Having $C_nH_{(2n-1)}$— Group

[Step 1]

Into a reactor, 64 g of tetrahydrofuran, 107 g of tris (trimethylsiloxy)silane, and 0.011 g of palladium carbon (30 wt %, supported on activated carbon) were added. This was cooled with ice-water bath to the bulk temperature of 10° C. or less. To this, 9.45 g of water was added. Then, this was stirred at a bulk temperature of 5 to 10° C. for 1 hour, and subsequently rising the temperature slowly, stirred at 25° C. for 12 hours. The reactant solution was filtered through a filter paper, and the solvent was removed by an evaporator therefrom to give Compound A with a purity of 96%. The yield was 93%. This was subjected to FT-IR measurement to confirm that the object could be obtained on the basis of disappearance of a peak in a range of 2200 to 2300 cm$^{-1}$ and formation of a peak in a range of 3500 to 3700 cm$^{-1}$.

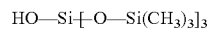  [Compound A]

[Step 2]

Into a reactor, 71.0 g of Compound A, 313 g of n-hexane, and 24.3 g of triethylamine were added. This was cooled with ice-water bath to the bulk temperature of 15° C. or less. To this, 28.8 g of dimethylvinylchlorosilane was added dropwise with the bulk temperature being held at 5 to 15° C. Then, this was stirred at a temperature of 20 to 23° C. for 12 hours. The reactant solution was washed with 400 g of water twice, and subsequently concentrated under reduced pressure to give Compound B with a purity of 98%. The yield was 88%.

$^1$HNMR: 6.09 to 6.19 ppm (1H, m), 5.89 to 5.99 ppm (1H, d), 5.70 to 5.79 ppm (1H, d), −0.18 to 0.32 ppm (33H, m)

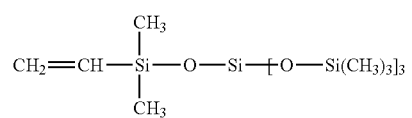

[Compound B]

Synthesis Example 2

[Step 1]

Into a 3000 ml of a separable flask equipped with a stirrer, a reflux condenser, a dropping funnel, and a thermometer, 500 g of tetrahydrofuran, 122 g of water, and 0.3 g of palladium carbon (30 wt %, supported on activated carbon) were added. This was cooled with ice-water bath to the bulk temperature of 10° C. or less. To this, 500 g of 1,1,1,3,5,5, 5-heptamethyltrisiloxane was added dropwise with the bulk temperature being held at 5 to 10° C. Then, this was stirred at 25° C. for 6 hours. The reactant solution was filtered through a filter paper, concentrated under reduced pressure, and distilled to give Compound C with a purity of 98.4% as a distillate at a boiling point of 91 to 99° C./42 to 43 mmHg. The yield was 92%. This was subjected to FT-IR measurement to confirm that the object could be obtained on the basis of disappearance of a peak in a range of 2100 to 2200 cm$^{-1}$ and formation of a peak in a range of 3500 to 3700 cm$^{-1}$.

[Compound C]

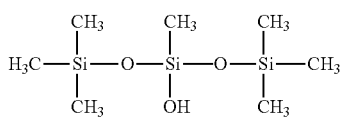

Into a 2000 ml of a separable flask equipped with a stirrer, a reflux condenser, a dropping funnel, and a thermometer, 308.8 g of Compound C, 500 g of n-hexane, and 124.4 g of triethylamine were added. This was cooled with ice-water bath to the bulk temperature of 15° C. or less. To this, 86 g of methylvinyldichlorosilane was added dropwise with the bulk temperature being held at 5 to 10° C. Then, this was stirred at a temperature of 15 to 20° C. for 12 hours. The reactant solution was washed with 400 g of water twice. The solvent was evaporated therefrom with an evaporator to give Compound D with a purity of 95%. The yield was 97%.

$^{1}$HNMR: 6.09 to 6.19 ppm (1H, m), 5.89 to 5.99 ppm (1H, d), 5.70 to 5.79 ppm (1H, d), −0.18 to 0.32 ppm (45H, m)

[Compound D]

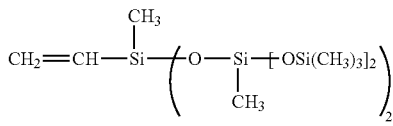

Example 1

Into a reactor, 100 g of organohydrogensiloxane shown by the following average composition formula (11) and 21.47 g of the foregoing Compound B were introduced, and 0.05 g of 0.3% by mass isopropyl alcohol solution of chloroplatinic acid was added. This was reacted at a bulk temperature of 80° C. for 1 hour.

Then, 38.54 g of polyoxyalkylene shown by the following average composition formula (12), 50 g of isopropyl alcohol, and 0.08 g of 0.3% by mass isopropyl alcohol solution of chloroplatinic acid were added, and reacted for 5 hours under reflux of the solvent. The reactant was heated under reduced pressure to evaporate the solvent to give a silicone compound shown by the following average composition formula (13) with a weight-average molecular weight of 6000 in a yield of 90%.

(11)

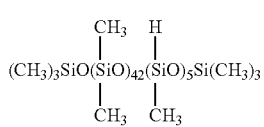

(12)

$CH_2$=$CHCH_2O(C_2H_4O)_9H$ (13)

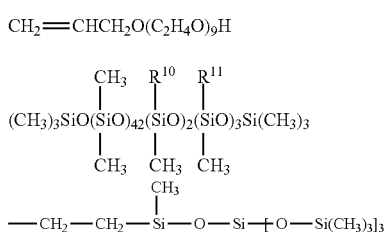

Example 2

Into a reactor, 100 g of organohydrogensiloxane shown by the foregoing average composition formula (11), 10.74 g of the foregoing Compound B, and 17.2 g of organosiloxane shown by the following average composition formula (14) were introduced, and 0.05 g of 0.3% by mass isopropyl alcohol solution of chloroplatinic acid was added. This was reacted at a bulk temperature of 80° C. for 1 hour.

Then, 38.54 g of polyoxyalkylene shown by the average composition formula (12), 50 g of isopropyl alcohol, and 0.08 g of 0.3% by mass isopropyl alcohol solution of chloroplatinic acid were added, and reacted for 5 hours under reflux of the solvent. The reactant was heated under reduced pressure to evaporate the solvent to give a silicone compound shown by the following average composition formula (15) with a weight-average molecular weight of 6500 in a yield of 92%.

(14)

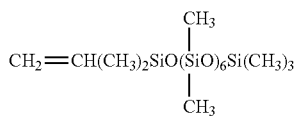

(15)

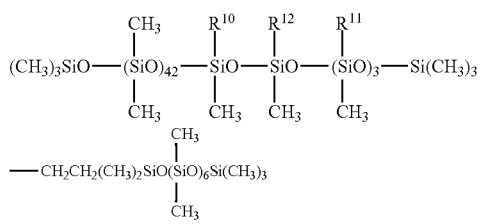

Example 3

In a reactor, 416 g of organohydrogensiloxane shown by the following average composition formula (16), 910 g of polyoxyalkylene shown by the average composition formula (12), and 600 g of isopropyl alcohol were mixed, and 0.2 g of 2% by mass isopropyl alcohol solution of chloroplatinic acid was added thereto. This was reacted for 6 hours under reflux of the solvent. Then, 238 g of Compound B was added thereto, and the reaction was continued.

(16)

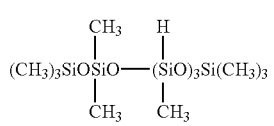

After performing the reaction for 6 hours under reflux of the solvent, 67 g of 1-dodecene was added, and heated to reflux for 3 hours to complete the reaction. The unreacted Si—H group was hydrolyzed by adding 4.2 g of 5% aqueous sodium hydroxide. Then, this was neutralized by adding 0.5 g of concentrated hydrochloric acid. Furthermore, 214 g of 0.01 N aqueous hydrochloric acid solution was added to hydrolyze the unreacted allyl ether group of the polyoxyalkylene, and this was neutralized with 3.6 g of 5% by mass aqueous sodium hydrogencarbonate.

The reactant was heated under reduced pressure to evaporate the solvent, and then subjected to filtration to give organopolysiloxane shown by the following average composition formula (17) with a weight-average molecular weight of 1800 in a yield of 89%.

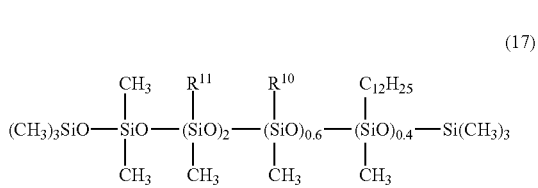

(17)

Example 4

In a reactor, 652 g of organohydrogensiloxane shown by the following average composition formula (18), 247 g of polyoxyalkylene shown by the average composition formula (12), and 600 g of isopropyl alcohol were mixed, and 0.2 g of 2% by mass isopropyl alcohol solution of chloroplatinic acid was added thereto. This was reacted for 6 hours under reflux of the solvent.

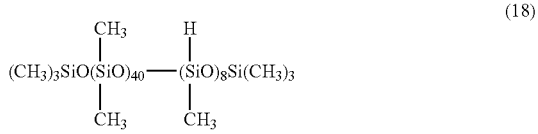

(18)

Furthermore, 144 g of Compound B was added, and the reaction was continued. After performing the reaction for 6 hours under reflux of the solvent, 93 g of 1-dodecene was added, and heated to reflux for 3 hours to complete the reaction. The unreacted Si—H group was hydrolyzed by adding 6.5 g of 5% by mass aqueous sodium hydroxide. Then, this was neutralized by adding 0.8 g of concentrated hydrochloric acid. Furthermore, 192 g of 0.01 N aqueous hydrochloric acid solution was added to hydrolyze the unreacted allyl ether group of the polyoxyalkylene, and this was neutralized with 3.2 g of 5% by mass aqueous sodium hydrogencarbonate.

The reactant was heated under reduced pressure to evaporate the solvent, and then subjected to filtration to give organopolysiloxane shown by the following average composition formula (19) with a weight-average molecular weight of 6500 in a yield of 90%.

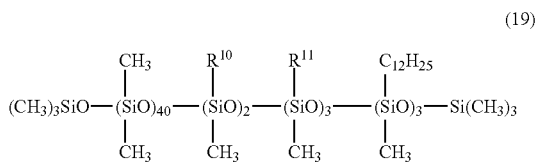

(19)

Example 5

In a reactor, 394 g of organohydrogensiloxane shown by the following average composition formula (20), 38 g of Compound D, 116 g of polyoxyalkylene shown by the following average composition formula (21), and 1000 g of isopropyl alcohol were mixed, and 0.4 g of 2% by mass isopropyl alcohol solution of chloroplatinic acid was added thereto. This was reacted for 6 hours under reflux of the solvent.

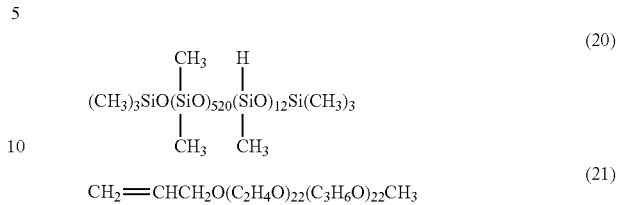

(20)

(21)

The reactant was heated under reduced pressure to evaporate the solvent to give organopolysiloxane shown by the following average composition formula (22) with a weight-average molecular weight of 60000 in a yield of 85%.

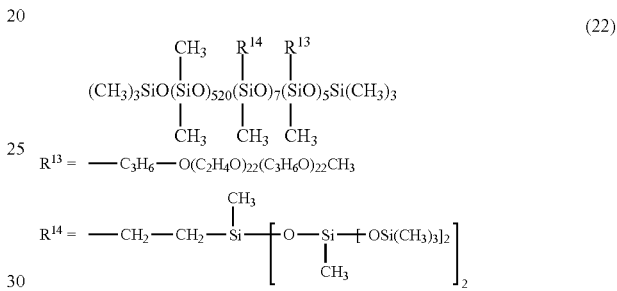

(22)

Comparative Example 1

Into a reactor, 714 g of organohydrogensiloxane shown by the average composition formula (11) and 247 g of organosiloxane shown by the average composition formula. (14) were introduced, and 0.1 g of 3% by mass isopropyl alcohol solution of chloroplatinic acid was added thereto. This was reacted at a bulk temperature of 80° C. for 1 hour.

Then, 291 g of polyoxyalkylene shown by the average composition formula (12), 640 g of isopropyl alcohol, and 0.8 g of 3% by mass isopropyl alcohol solution of chloroplatinic acid were added, and reacted for 5 hours under reflux of the solvent. Subsequently, the reactant was heated under reduced pressure to evaporate the solvent to give a silicone compound shown by the following average composition formula (23) with a weight-average molecular weight of 6200 in a yield of 90%.

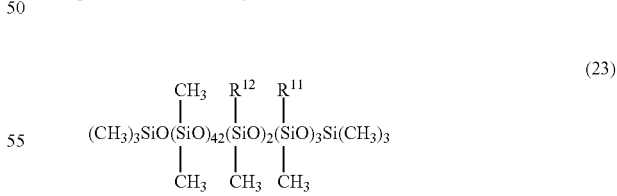

(23)

Comparative Example 2

Into a reactor, 714 g of organohydrogensiloxane shown by the average composition formula (11) and 129 g of vinyltris(trimethylsiloxy)silane were introduced, and 0.8 g of 0.3% by mass isopropyl alcohol solution of chloroplatinic acid was added thereto. This was reacted at a bulk temperature of 80° C. for 1 hour.

Then, 291 g of polyoxyalkylene shown by the average composition formula (12), 640 g of isopropyl alcohol, and 0.8 g of 3% by mass isopropyl alcohol solution of chloroplatinic acid were added, and reacted for 5 hours under reflux of the solvent. Subsequently, the reactant was heated under reduced pressure to evaporate the solvent to give a silicone compound shown by the following average composition formula (24) with a weight-average molecular weight of 6500 in a yield of 90%.

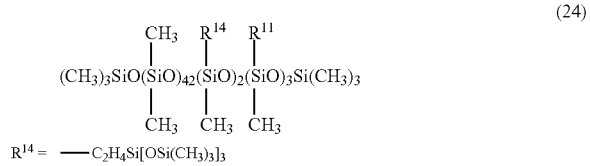
(24)

$R^{14} = \text{---} C_2H_4Si[OSi(CH_3)_3]_3$

Examples 6 to 9, Comparative Examples 3 and 4

Water-in-oil type emulsions were prepared on the basis of the formulations shown in the following Table 1, and evaluated by the evaluation methods and criteria shown below. These results are also shown in Table 1.

Excellent: uniform emulsion with no separation
Good: no separation with slight light and shade
Fair: slight separation of oil in the upper layer
Poor: separation was confirmed 2. Organoleptic Evaluation
<1> Spreading Property at Application
<2> Smoothness of Skin after Application
(Evaluation Method)

Each sample was tried by 20 professional panelists to be evaluated on <1> spreading property at application and <2> smoothness of skin after application on the basis of the following criteria.
5 points: good
4 points: fair
3 points: medium
2 points: rather poor
1 point: poor From the average point of the evaluation obtained above, the samples were decided on the basis of the following criteria. The results are shown in Table 1. Decision of the average point:

| | |
|---|---|
| The obtained average point is 4.5 points or more | A |
| The obtained average point is 3.5 points or more and less than 4.5 points | B |
| The obtained average point is 2.5 points or more and less than 3.5 points | C |
| The obtained average point is 1.5 points or more and less than 2.5 points | D |
| The obtained average point is less than 1.5 points | E |

TABLE 1

| | Ingredients and Properties | Examples | | | | Comparative Examples | |
|---|---|---|---|---|---|---|---|
| | | 6 | 7 | 8 | 9 | 3 | 4 |
| 1 | Silicone compound (13) | 2 | 1 | 0.5 | | | |
| | Silicone compound (15) | | | | 2 | | |
| | Silicone compound (23) | | | | | 2 | |
| | Silicone compound (24) | | | | | | 2 |
| 2 | Dimethylpolysiloxane (6 mm²/s) | 25 | 25 | 25 | 25 | 25 | 25 |
| 3 | Sodium chloride | 0.5 | 0.5 | 0.5 | 0.5 | 0.5 | 0.5 |
| 4 | 1,3-Butylene glycol | 5 | 5 | 5 | 5 | 5 | 5 |
| 5 | Purified water | 69.5 | 69.5 | 69.5 | 69.5 | 69.5 | 69.5 |
| | Stability (immediately after preparation) | Excellent | Excellent | Excellent | Excellent | Excellent | Excellent |
| | Stability (50° C./1 day) | Excellent | Excellent | Excellent | Excellent | Good | Excellent |
| | Stability (50° C./3 day) | Excellent | Excellent | Good | Excellent | Fair | Good |
| | Stability (50° C./8 day) | Excellent | Excellent | Fair | Excellent | Poor | Good |
| | Stability (50° C./14 day) | Excellent | Excellent | Fair | Good | Poor | Fair |
| | <1> Spreading property at application | A | A | B | A | D | C |
| | <2> Smoothness of skin after application | A | A | B | B | D | C |

[Preparation Method of Water-in-Oil Type Emulsion]
A. Ingredients 1 to 2 were blended uniformly.
B. Ingredients 3 to 5 were blended uniformly.
C. The mixture obtained in B was added to the mixture obtained in A with stirring to form an emulsion.

[Evaluation Criteria]
1. Temporal Stability
(Evaluation Method)

Emulsion stabilities were evaluated by visual observation of the appearance at immediately after the preparation; and after storing at 50° C. for 1 day, 3 days, 8 days, and 14 days on the basis of the following criteria.

As shown in Table 1, it has been confirmed that Examples 6, 7, and 9 is superior to Comparative Examples 3 and 4 in temporal stability, spreading property at application, and smoothness of skin after application. Example 8, in which the content was lowered to a quarter, showed the same or higher stability than Comparative Example 3, and showed superior usability compared to Comparative Examples 3 and 4.

The following shows formulation examples of the cosmetics.

(Formulation Example 1) Emulsified Cream Foundation

| (Ingredients) | Mass (%) |
|---|---|
| 1. Alkyl modified crosslink type polyether modified silicone (*1) | 2.0 |
| 2. Alkyl modified crosslink type dimethylpolysiloxane (*2) | 2.0 |
| 3. Liquid paraffin | 2.0 |
| 4. Trioctanoin | 5.0 |
| 5. Isotridecyl isononanate | 9.0 |
| 6. Silicone compound (19) | 1.5 |
| 7. Hybrid silicone composite powder (*3) | 3.0 |
| 8. Triethoxysilyl ethyl polydimethylsiloxy ethylhexyl dimethicone (*4) treated iron oxide | 2.5 |
| 9. Triethoxysilyl ethyl polydimethylsiloxy ethylhexyl dimethicone (*4) treated titanium oxide | 7.5 |
| 10. 1,3-Butylene glycol | 5.0 |
| 11. Sodium citrate | 3.0 |
| 12. Magnesium sulfate | 3.0 |
| 13. Preservative | appropriate |
| 14. Perfume | appropriate |
| 15. Purified water | remainder |
| Sum: 100.0 | |

(*1) KSG-310 (manufactured by Shin-Etsu Chemical Co., Ltd.)
(*2) KSG-41 (manufactured by Shin-Etsu Chemical Co., Ltd.)
(*3) KSP-100 (manufactured by Shin-Etsu Chemical Co., Ltd.)
(*4) KF-9909 (manufactured by Shin-Etsu Chemical Co., Ltd.)

(Production Method)
A: Ingredients 1 to 6 were mixed uniformly, and then blended with Ingredients 7 to 9 to form a uniform mixture.
B: Ingredients 10 to 13 were dissolved into 15.
C: The mixture obtained in B was gradually added to the mixture obtained in A with stirring to form an emulsion. After cooling the emulsion, Ingredient 14 was added to give emulsified cream foundation.

The emulsified cream foundation thus obtained was confirmed as having a low viscosity and fine texture, a light spreading property with no stickiness nor greasiness, and showing a soft use feeling, a favorable skin corrective effect, cosmetic durability, and excellent stability with no change due to temperature change nor a change with the passage of time.

(Formulation Example 2) Water-in-Oil Type Cream

| (Ingredients) | Mass (%) |
|---|---|
| 1. Alkyl modified crosslink type polyether modified silicone (*1) | 6.0 |
| 2. Alkyl modified crosslink type dimethylpolysiloxane (*2) | 2.0 |
| 3. Liquid paraffin | 13.5 |
| 4. *Macadamia* nut oil | 5.0 |
| 5. Silicone compound (19) | 1.0 |
| 6. Hybrid silicone composite powder (*3) | 3.0 |
| 7. Sodium citrate | 0.2 |
| 8. Dipropylene glycol | 8.0 |
| 9. Glycerin | 3.0 |
| 10. Preservative | appropriate |
| 11. Perfume | appropriate |
| 12. Purified water | remainder |
| Sum: 100.0 | |

(*1) KSG-310 (manufactured by Shin-Etsu Chemical Co., Ltd.)
(*2) KSG-41 (manufactured by Shin-Etsu Chemical Co., Ltd.)
(*3) KSP-100 (manufactured by Shin-Etsu Chemical Co., Ltd.)

(Production Method)
A: Ingredients 1 to 6 were mixed with each other.
B: Ingredients 7 to 11 were dissolved into 12 with mixing, and then the mixture was added to the mixture obtained in A. This was stirred and emulsified to give water-in-oil type cream.

The water-in-oil type cream thus obtained was confirmed as having fine texture, a light spreading property with no stickiness nor greasiness, and showing a soft use feeling, a favorable skin corrective effect, very good cosmetic durability, and excellent stability with no change due to temperature change nor a change with the passage of time.

(Formulation Example 3) Water-in-Oil Type Cream

| (Ingredients) | Mass (%) |
|---|---|
| 1. Decamethylcyclopentasiloxane | 16.0 |
| 2. Dimethylpolysiloxane (6 mm$^2$/s (25° C.)) | 4.0 |
| 3. Silicone compound (13) | 5.0 |
| 4. POE (5) octyl dodecyl ether | 1.0 |
| 5. Polyoxyethylene sorbitan monostearate (20 E.O.) | 0.5 |
| 6. Hybrid silicone composite powder (*1) | 2.0 |
| 7. Plate-like barium sulfate (*2) | 2.0 |
| 8. Liquid paraffin | 2.0 |
| 9. *Macadamia* nut oil | 1.0 |
| 10. *Scutellaria baicalensis* root extract (*3) | 1.0 |
| 11. Gentian extract (*4) | 0.5 |
| 12. Ethanol | 5.0 |
| 13. 1,3-Butylene glycol | 2.0 |
| 14. Preservative | appropriate |
| 15. Perfume | appropriate |
| 16. Purified water | remainder |
| Sum: 100.0 | |

(*1) KSP-411 (manufactured by Shin-Etsu Chemical Co., Ltd.)
(*2) HL (manufactured by SAKAI CHEMICAL INDUSTRY CO., LTD.)
(*3) extracted with 50% aqueous 1,3-butylene glycol
(*4) extracted with 20% aqueous ethanol (Production Method)
A: Ingredients 6 to 9 were mixed to form a uniform dispersion.
B: Ingredients 1 to 5 were mixed and blended with the mixture obtained in A.
C: Ingredients 10 to 14 and 16 were mixed, and then blended with the mixture obtained in B to form an emulsion.
D: Ingredient 15 was added to the mixture obtained in C to give water-in-oil type cream.

The water-in-oil cream thus obtained was confirmed as having fine texture with no stickiness, and showing a light spreading property, an excellent adhesion feeling, a soft use feeling, a favorable skin corrective effect, and very good cosmetic durability, as well as excellent stability with no change due to temperature change nor a change with the passage of time.

(Formulation Example 4) Eye Liner

| (Ingredients) | Mass (%) |
|---|---|
| 1. Decamethylcyclopentasiloxane | 39.0 |
| 2. Silicone compound (15) | 3.0 |
| 3. Organic silicone resin (*1) | 15.0 |
| 4. Dioctadecyldimethylammonium salt modified montmorillonite | 3.0 |
| 5. Methylhydrogenpolysiloxane treated black iron oxide | 10.0 |
| 6. 1,3-Butylene glycol | 5.0 |
| 7. Sodium dehydroacetate | appropriate |
| 8. Preservative | appropriate |
| 9. Purified water | remainder |
| | Sum: 100.0 |

(*1) KF-7312J (manufactured by Shin-Etsu Chemical Co., Ltd.)

(Production Method)
A: Ingredients 1 to 4 were mixed, blended with Ingredient 5, and mixed to form a uniform dispersion.
B: Ingredients 6 to 9 were mixed with each other.
C: The mixture obtained in B was gradually added to the mixture obtained in A, and emulsified to give eye liner.

The eye liner thus obtained had a light spreading property and thus is easy to draw as well as a cool and fresh use feeling without stickiness. The eye liner was also confirmed as having excellent water-resistance and perspiration resistance with very good cosmetic durability as well as excellent usability and stability with no change due to temperature change nor a change with the passage of time.

(Formulation Example 5) Foundation

| (Ingredients) | Mass (%) |
|---|---|
| 1. Decamethylcyclopentasiloxane | 45.0 |
| 2. Dimethylpolysiloxane (6 mm$^2$/s (25° C.)) | 5.0 |
| 3. Silicone compound (13) | 3.5 |
| 4. Octadecyldimethylbenzylammonium salt modified montmorillonite | 1.5 |
| 5. Hybrid silicone composite powder (*1) | 2.0 |
| 6. Triethoxysilylehtyl polydimethylsiloxyethyl hexyl dimethicone (*2) treated iron oxide | 2.5 |
| 7. Triethoxysilylehtyl polydimethylsiloxyethyl hexyl dimethicone (*2) treated titanium oxide | 7.5 |
| 8. Dipropylene glycol | 5.0 |
| 9. Methyl p-oxybenzoate ester | 0.3 |
| 10. Perfume | appropriate |
| 11. Purified water | remainder |
| | Sum: 100.0 |

(*1) KSP-105 (manufactured by Shin-Etsu Chemical Co., Ltd.)
(*2) KF-9909 (manufactured by Shin-Etsu Chemical Co., Ltd.)

(Production Method)
A: Ingredients 1 to 4 were mixed with heating, and then blended with Ingredients 5 to 7 to form a uniform mixture.
B: Ingredients 8 to 9 were dissolved into Ingredient 11.
C: The mixture obtained in B was gradually added to the mixture obtained in A with stirring to form an emulsion. This emulsion was cooled, and then blended with Ingredient 10 to give foundation.

The foundation thus obtained was confirmed as having fine texture and a light spreading property with no stickiness nor greasiness, and showing a soft use feeling, a favorable skin corrective effect, good cosmetic durability, and excellent stability with no change due to temperature change nor a change with the passage of time.

(Formulation Example 6) Cream Eye Shadow

| (Ingredients) | Mass (%) |
|---|---|
| 1. Decamethylcyclopentasiloxane | 15.0 |
| 2. Dimethylpolysiloxane (6 mm$^2$/s (25° C.)) | 4.0 |
| 3. Acryl silicone resin (*1) | 5.0 |
| 4. Silicone compound (15) | 1.5 |
| 5. Acryl silicone resin treated pigment (*2) | 16.0 |
| 6. Sodium chloride | 2.0 |
| 7. Propylene glycol | 8.0 |
| 8. Preservative | appropriate |
| 9. Purified water | 48.5 |
| | Sum: 100.0 |

(*1) KP-545L (manufactured by Shin-Etsu Chemical Co., Ltd.)
(*2) treated with KP-574 (manufactured by Shin-Etsu Chemical Co., Ltd.)

(Production Method)
A: Ingredients 1 to 4 were mixed, and then blended with Ingredients 5 to form a uniformly mixed dispersion.
B: Ingredients 6 to 9 were mixed with each other.
C: The mixture obtained in B was added to the mixture obtained in A, and emulsified to give cream eye shadow.

The cream eye shadow thus obtained showed a light spreading property with no oiliness nor powderiness, and also had cosmetic durability.

(Formulation Example 7) Sun Cut Cream

| (Ingredients) | Mass (%) |
|---|---|
| 1. Crosslink type polyether modified silicone (*1) | 3.0 |
| 2. Crosslink type dimethylpolysiloxane (*2) | 2.0 |
| 3. Silicone compound (13) | 1.0 |
| 4. Acryl silicone resin (*3) | 7.0 |
| 5. Decamethylcyclopentasiloxane | 15.5 |
| 6. Octyl methoxycinnamate | 6.0 |
| 7. Solved acryl silicone resin (*4) | 10.0 |
| 8. Lipophilic treated microparticle zinc oxide (*5) | 20.0 |
| 9. 1,3-Butylene glycol | 2.0 |
| 10. Sodium citrate | 0.2 |
| 11. Sodium chloride | 0.5 |
| 12. Perfume | appropriate |
| 13. Purified water | 32.8 |
| | Sum: 100.0 |

(*1) KSG-240 (manufactured by Shin-Etsu Chemical Co., Ltd.)
(*2) KSG-15 (manufactured by Shin-Etsu Chemical Co., Ltd.)
(*3) KF-545 (manufactured by Shin-Etsu Chemical Co., Ltd.)
(*4) KP-575 (manufactured by Shin-Etsu Chemical Co., Ltd.)
(*5) treated with AES-3083 (manufactured by Shin-Etsu Chemical Co., Ltd.)

(Production Method)
A: Ingredient 7 was added to part of Ingredient 5, and mixed uniformly. Then, Ingredient 8 was added thereto and dispersed with a bead mill.
B: Ingredients 1 to 4, Ingredient 6, and remainder of Ingredient 5 were mixed uniformly.
C: Ingredients 9 to 11 and Ingredient 13 were mixed uniformly.
D: The mixture obtained in C was added to the mixture obtained in B to form an emulsion, and then blended with the mixture obtained in A and Ingredient 12 to give sun cut cream.

The sun cut cream thus obtained gave a light spreading property with no stickiness and a fresh use feeling no oiliness, and had good cosmetic durability.

(Formulation Example 8) Sun Cut Cream

| (Ingredients) | Mass (%) |
| --- | --- |
| 1. Crosslink type polyether modified silicone (*1) | 2.0 |
| 2. Crosslink type dimethylpolysiloxane (*2) | 3.0 |
| 3. Silicone compound (15) | 1.5 |
| 4. Acryl silicone resin (*3) | 4.5 |
| 5. Decamethylcyclopentasiloxane | 5.8 |
| 6. Dimethyldistearylammonium hectorite | 1.2 |
| 7. Titanium oxide dispersion (*4) | 20.0 |
| 8. Zinc oxide dispersion (*5) | 15.0 |
| 9. 1,3-Butylene glycol | 5.0 |
| 10. Sodium citrate | 0.2 |
| 11. Sodium chloride | 0.5 |
| 12. Purified water | 41.3 |
| | Sum: 100.0 |

(*1) KSG-210 (manufactured by Shin-Etsu Chemical Co., Ltd.)
(*2) KSG-15 (manufactured by Shin-Etsu Chemical Co., Ltd.)
(*3) KP-549 (manufactured by Shin-Etsu Chemical Co., Ltd.)
(*4) SPD-T6 (manufactured by Shin-Etsu Chemical Co., Ltd.)
(*5) SPD-Z6 (manufactured by Shin-Etsu Chemical Co., Ltd.)

(Production Method)
A: Ingredients 1 to 8 were mixed uniformly.
B: Ingredients 9 to 12 were mixed with each other.
C: The mixture obtained in B was added to the mixture obtained in A, and emulsified to give sun cut cream.

The sun cut cream thus obtained showed a light spreading property with no stickiness nor greasiness, and had good cosmetic durability.

(Formulation Example 9) Suntan Cream

| (Ingredients) | Mass (%) |
| --- | --- |
| 1. Alkyl modified crosslink type polyether modified silicone (*1) | 4.0 |
| 2. alkyl modified crosslink type dimethylpolysiloxane (*2) | 2.0 |
| 3. Silicone compound (22) | 1.0 |
| 4. Organic silicone resin (*3) | 5.0 |
| 5. Decamethylcyclopentasiloxane | 10.5 |
| 6. Stearyl modified acryl silicone (*4) | 1.0 |
| 7. Dimethyloctyl-p-aminobenzoic acid | 1.5 |
| 8. 4-t-butyl-4'-methoxy-dibenzoylmethane | 1.5 |
| 9. Kaolin | 0.5 |
| 10. Pigment | 8.0 |
| 11. Mica coated with titanium oxide | 8.0 |
| 12. Dioctadecyldimethylammonium chloride | 0.1 |
| 13. Sodium L-glutamate | 3.0 |
| 14. 1,3-Butylene glycol | 5.0 |
| 15. Sodium citrate | 0.2 |
| 16. Sodium chloride | 0.5 |
| 17. Antioxidant | appropriate |
| 18. Preservative | appropriate |
| 19. Perfume | appropriate |
| 20. Purified water | remainder |
| | Sum: 100.0 |

(*1) KSG-320 (manufactured by Shin-Etsu Chemical Co., Ltd.)
(*2) KSG-42 (manufactured by Shin-Etsu Chemical Co., Ltd.)
(*3) KF-7312J (manufactured by Shin-Etsu Chemical Co., Ltd.)
(*4) KP-561P (manufactured by Shin-Etsu Chemical Co., Ltd.)

(Production Method)
A: Ingredients 1 to 8, 17, and 18 were mixed with heating.
B: Ingredient 12 and part of Ingredient 20 were stirred with heating, blended with Ingredients 9 to 11, and then subjected to dispersing treatment.
C: Ingredients 13 to 16 were dissolved uniformly into the remainder of Ingredient 20, and then blended with the mixture obtained in B.
D: The mixture obtained in C was gradually added to the mixture obtained in A with stirring to form an emulsion. After cooling the emulsion, Ingredient 19 was added to give suntan cream.

The suntan cream thus obtained had fine texture, a light spreading property with no stickiness nor greasiness, and gave a fresh use feeling and durability.

(Formulation Example 10) Hair Cream

| (Ingredients) | Mass (%) |
| --- | --- |
| 1. Decamethylcyclopentasiloxane | 16.0 |
| 2. Methylphenylpolysiloxane (*1) | 2.0 |
| 3. Organic silicone resin (*2) | 4.0 |
| 4. Squalane | 5.0 |
| 5. Acryl silicone resin (*3) | 2.0 |
| 6. Sorbitan sesquiisostearate | 1.5 |
| 7. Silicone compound (22) | 2.0 |
| 8. Sorbitol sodium sulfate | 2.0 |
| 9. Chondroitin sulfate sodium salt | 1.0 |
| 10. Hyaluronic acid sodium salt | 0.5 |
| 11. Propylene glycol | 3.0 |
| 12. Preservative | 1.5 |
| 13. Vitamin E acetate | 0.1 |
| 14. Antioxidant | appropriate |
| 15. Perfume | appropriate |
| 16. Purified water | remainder |
| | Sum: 100.0 |

(*1) KF-54 (manufactured by Shin-Etsu Chemical Co., Ltd.)
(*2) KF-7312T (manufactured by Shin-Etsu Chemical Co., Ltd.)
(*3) KP-545 (manufactured by Shin-Etsu Chemical Co., Ltd.)

(Production Method)
A: Ingredients 1 to 7 and Ingredients 12 to 14 were mixed uniformly.
B: Ingredients 8 to 11 and Ingredient 16 were mixed uniformly.
C: The mixture obtained in B was gradually added to the mixture obtained A with stirring to form an emulsion, and then blended with Ingredient 15 to give hair cream.

The hair cream thus obtained showed a light spreading property with no greasiness, and had water-resistance, repellency, perspiration resistance, and good durability.

(Formulation Example 11) O/W Type Cream

| (Ingredients) | Mass (%) |
| --- | --- |
| 1. Crosslink type dimethylpolysiloxane (*1) | 8.0 |
| 2. Crosslink type methylphenylpolysiloxane (*2) | 2.0 |
| 3. Isotridecyl isononanate | 5.0 |
| 4. Dipropylene glycol | 7.0 |
| 5. Glycerin | 5.0 |
| 6. Methyl cellulose (2% aqueous solution) (*3) | 7.0 |
| 7. Polyacrylamide type emulsifier (*4) | 2.0 |
| 8. Silicone compound (17) | 0.5 |
| 9. Guanine | 1.0 |

-continued

| | (Ingredients) | Mass (%) |
|---|---|---|
| 10. | Preservative | 0.1 |
| 11. | Perfume | 0.1 |
| 12. | Purified water | remainder |
| | | Sum: 100.0 |

(*1) KSG-16 (manufactured by Shin-Etsu Chemical Co., Ltd.)
(*2) KSG-18A (manufactured by Shin-Etsu Chemical Co., Ltd.)
(*3) METOLOSE SM-4000 (manufactured by Shin-Etsu Chemical Co., Ltd.)
(*4) SEPIGEL 305 (manufactured by SEPPIC)

(Production Method)

A: Ingredients 1 to 3 were mixed uniformly.

B: Ingredients 4 to 10 and 12 were mixed uniformly.

C: The mixture obtained in A was gradually added to the mixture obtained in B with stirring to form an emulsion, and then blended with Ingredient 11 to give cream.

The cream thus obtained was found to be an O/W type cream having fine texture, a light spreading property with no stickiness nor greasiness, and giving a moistening and a refreshing feeling, a fresh use feeling, very good cosmetic durability and excellent stability with no change due to temperature change nor a change with the passage of time.

(Formulation Example 12) O/W Emollient Cream

| | (Ingredients) | Mass (%) |
|---|---|---|
| 1. | Crosslink type dimethylpolysiloxane (*1) | 7.0 |
| 2. | Crosslink type dimethylpolysiloxane (*2) | 30.0 |
| 3. | Acryl silicone resin (*3) | 3.0 |
| 4. | Decamethylcyclopentasiloxane | 8.0 |
| 5. | 1,3-Butylene glycol | 4.0 |
| 6. | Branched type polygrycerin modified silicone (*4) | 0.6 |
| 7. | Silicone compound (17) | 0.3 |
| 8. | Copolymer of acrylamide/Na acryloyldimethyltaurate (*5) | 0.6 |
| 9. | Copolymer of ammonium acryloyldimethyltaurate/VP (*6) | 0.7 |
| 10. | Sodium chloride | 0.1 |
| 11. | Purified water | 45.7 |
| | | Sum: 100.0 |

(*1) KSG-15 (manufactured by Shin-Etsu Chemical Co., Ltd.)
(*2) KSG-16 (manufactured by Shin-Etsu Chemical Co., Ltd.)
(*3) KP-545 (manufactured by Shin-Etsu Chemical Co., Ltd.)
(*4) KF-6104 (manufactured by Shin-Etsu Chemical Co., Ltd.)
(*5) Simugel 600 (manufactured by SEPPIC)
(*6) Aristoflex AVC (manufactured by CLARIANT)

(Production Method)

A: Ingredients 1 to 4 were mixed uniformly.

B: Ingredients 5 to 11 were mixed uniformly.

C: The mixture obtained in A was gradually added to the mixture obtained in B with stirring and mixed with each other to give O/W emollient cream.

The O/W emollient cream thus obtained showed smoothness with no greasiness, had a light spreading property, and maintained an effect to protect skin.

(Formulation Example 13) Lip Stick

| | (Ingredients) | Mass (%) |
|---|---|---|
| 1. | Candelilla wax | 8.0 |
| 2. | Polyethylene wax | 8.0 |
| 3. | Long-chain alkyl-containing acryl silicone resin (*1) | 12.0 |
| 4. | Methylphenylpolysiloxane (*2) | 3.0 |
| 5. | Isotridecyl isononanate | 20.0 |
| 6. | Glyceryl isostearate | 16.0 |
| 7. | Silicone compound (19) | 0.5 |
| 8. | Octadecyldimethylbenzylammonium salt modified montmorillonite | 0.5 |
| 9. | Polyglyceryl triisostearate | 27.3 |
| 10. | Silicone (*3) treated Red No. 202 | 0.8 |
| 11. | Silicone (*3) treated red iron oxide | 1.5 |
| 12. | Silicone (*3) treated yellow iron oxide | 1.0 |
| 13. | Silicone (*3) treated black iron oxide | 0.2 |
| 14. | Silicone (*3) treated titanium oxide | 1.0 |
| 15. | Preservative | 0.1 |
| 16. | Perfume | 0.1 |
| | | Sum: 100.0 |

(*1) KP-561P (manufactured by Shin-Etsu Chemical Co., Ltd.)
(*2) KF-54 (manufactured by Shin-Etsu Chemical Co., Ltd.)
(*3) KP-541 (manufactured by Shin-Etsu Chemical Co., Ltd.)

(Production Method)

A: Ingredients 1 to 7 were mixed with heating to be dissolved with each other.

B: Ingredients 8 to 15 were mixed uniformly.

C: The mixture obtained in B was added to the mixture obtained in A, and then blended with Ingredient 16 to form a uniform mixture.

The lip stick thus obtained had shiny surface with light spreading property and with no oiliness nor powderiness, and gave a fresh use feeling, good water-resistance and repellency as well as good durability and excellent stability.

(Formulation Example 14) Powder Foundation

| | (Ingredients) | Mass (%) |
|---|---|---|
| 1. | Vaseline | 2.5 |
| 2. | Squalane | 3.0 |
| 3. | Silicone compound (19) | 0.5 |
| 4. | Glyceryl trioctanoate | 2.0 |
| 5. | Silicone (*1) treated mica | 40.0 |
| 6. | Silicone (*1) treated talc | 22.2 |
| 7. | Silicone (*1) treated titanium oxide | 10.0 |
| 8. | Silicone (*1) treated microparticle titanium oxide | 5.0 |
| 9. | Silicone (*1) treated barium sulfate | 10.0 |
| 10. | Pigment | 0.1 |
| 11. | Phenyl modified hybrid silicone composite powder (*2) | 2.0 |
| 12. | silicone powder (*3) | 2.5 |
| 13. | Preservative | 0.1 |
| 14. | Perfume | 0.1 |
| | | Sum: 100.0 |

(*1) KP-541 (manufactured by Shin-Etsu Chemical Co., Ltd.)
(*2) KSP-300 (manufactured by Shin-Etsu Chemical Co., Ltd.)
(*3) KMP-590 (manufactured by Shin-Etsu Chemical Co., Ltd.)

(Production Method)

A: Ingredients 5 to 12 were mixed uniformly.

B: Ingredients 1 to 4 and 13 were mixed uniformly, and then blended with the mixture obtained in A.

C: The mixture was blended with Ingredient 14, and then press molded with a mold to give powder foundation.

The powder foundation thus obtained was found to be powder foundation having a light spreading property with no stickiness, and giving shiny finishing with excellent adhesion feeling and cosmetic durability.

(Formulation Example 15) Sunblock Milky Lotion

| (Ingredients) | Mass (%) |
|---|---|
| 1. Decamethylcyclopentasiloxane | 20.0 |
| 2. Methylphenylpolysiloxane | 3.0 |
| 3. Sorbitan monoisostearate | 1.0 |
| 4. Silicone compound (17) | 0.5 |
| 5. Trimethylsiloxysilicic acid (*1) | 1.0 |
| 6. Octyl p-methoxycinnamate | 4.0 |
| 7. Aluminum stearate treated microparticle titanium oxide | 7.0 |
| 8. Sorbitol | 2.0 |
| 9. Sodium chloride | 2.0 |
| 10. Preservative | appropriate |
| 11. Perfume | appropriate |
| 12. Purified water | remainder |
| Sum: | 100.0 |

(*1) X-21-5250 (manufactured by Shin-Etsu Chemical Co., Ltd.)

(Production Method)
A: Ingredients 1 to 6 were mixed with heating. Then, ingredient 7 was dispersed thereto uniformly.
B: Ingredients 8 to 10 and 12 were mixed with heating.
C: The mixture obtained in B was gradually added to the mixture obtained in A with stirring to form an emulsion. After cooling the emulsion, Ingredient 11 was added to give sunblock milky lotion.

The sunblock milky lotion thus obtained had fine texture, a light spreading property with no stickiness, and gave a soft use feeling, a favorable skin corrective effect. This lotion was confirmed as showing good cosmetic durability, thereby maintaining the ultraviolet protection effect, and having excellent stability with no change due to temperature change nor a change with the passage of time.

(Formulation Example 16) Cleansing Cream

| (Ingredients) | Mass (%) |
|---|---|
| 1. Dimethylpolysiloxane (6 mm²/s (25° C.)) | 5.0 |
| 2. Methylphenylpolysiloxane | 5.0 |
| 3. Liquid paraffin | 8.0 |
| 4. Jojoba oil | 2.0 |
| 5. Silicone compound (13) | 2.5 |
| 6. Silicone compound (17) | 0.5 |
| 7. Dextrin fatty acid ester | 0.8 |
| 8. Aluminum salt of monostearic acid | 0.2 |
| 9. Aluminum chloride | 1.0 |
| 10. Glycerin | 10.0 |
| 11. Preservative | appropriate |
| 12. Perfume | appropriate |
| 13. Purified water | remainder |
| Sum: | 100.0 |

(Production Method)
A: Ingredients 1 to 8 were mixed with heating.
B: Ingredients 9 to 11 and 13 were dissolved together with heating.
C: The mixture obtained in B was gradually added to the mixture obtained in A with stirring to form an emulsion. After cooling the emulsion, Ingredient 12 was added to give cleansing cream.

The cleansing cream thus obtained was found to have fine texture and a light spreading property with no stickiness nor greasiness, and to give moistening and a refreshing use feeling with a fresh use feeling as well as high cleansing effect and excellent stability with no change due to temperature change nor a change with the passage of time.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A silicone compound shown by the following average composition formula (1) and having a weight-average molecular weight in the range of 500 to 200,000, $$R^1_a R^2_b R^3_c R^4_d SiO_{(4-a-b-c-d)/2} \quad (1)$$

wherein "a", "b", "c", and "d" each represent a number satisfying $1.0 \leq a \leq 2.5$, $0.001 \leq b \leq 1.5$, $0.001 \leq c \leq 1.5$, and $0 \leq d \leq 1.0$;

$R^1$ represents the same or different organic group selected from an alkyl group having 1 to 30 carbon atoms;

$R^2$ represents the same or different polyoxyalkylene group shown by the general formula (3) $-C_m H_{2m}-O-(C_2H_4O)_g(C_3H_6O)_h R^6$, wherein $R^6$ represents a hydrogen atom or a hydrocarbon group having 1 to 30 carbon atoms; and "g" and "h" each represent an integer satisfying $2 \leq g \leq 200$, $0 \leq h \leq 200$, and g+h is 3 to 200; and "m" represents an integer satisfying $1 \leq m \leq 15$;

$R^3$ represents the same or different branched type monovalent organosiloxane group shown by the following general formula (4), $$M_o M^R_p D_q D^R_r T_s T^R_t Q_u \quad (4)$$

wherein $M=R^7_3 SiO_{0.5}$, $M^R=R^7_2 R^8 SiO_{0.5}$, $D=R^7_2 SiO$, $D^R=R^7 R^8 SiO$, $T=R^7 SiO_{1.5}$, $T^R=R^8 SiO_{1.5}$, and $Q=SiO_2$; $R^7$ represents the same or different organic group selected from an alkyl group having 1 to 30 carbon atoms; $R^8$ represents an organic group shown by $-C_n H_{2n}-$; "n" represents an integer satisfying $1 \leq n \leq 5$; "o" represents an integer of 1 or more; "q" and "s" each represent an integer of 0 or more; "p", "r", "t", and "u" each represent 0 or 1; with the proviso that "s", "t", and "u" are not equal to 0 at the same time, the sum of "p", "r", and "t" is 1, and when q=0, "o" is 2 or more and the sum of "s" and "u" is 1 or more;

$R^4$ represents the same or different monovalent organosiloxane group shown by the following general formula (5) or the general formula (6), $$MM^R D_{v-1} \quad (5)$$

$$M_w D_{v-1} D^R_{v-2} T^R_{v-3} \quad (6)$$

wherein M, $M^R$, D, $D^R$, and $T^R$ have the same meanings defined above; v-1 represents a number satisfying $0 \leq v-1 \leq 500$; v-2 and v-3 each represent 0 or 1; with the proviso that the sum of v-2 and v-3 is 1, and the both of v-1 and v-3 are not 1 or more at the same time; and "w" represents an integer of 2 to 3.

2. The silicone compound according to claim 1, wherein the silicone compound is shown by the following structural formula (1-1),

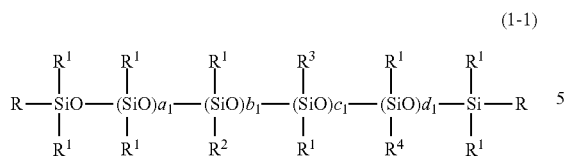

(1-1)

wherein $R^1$, $R^2$, $R^3$, and $R^4$ have the same meanings as defined above; R represents the same or different group selected from $R^1$, $R^2$, $R^3$, and $R^4$; a1 represents a number in a range of 0 to 1000, b1 represents a number in a range of 0 to 200, c1 represents a number in a range of 0 to 200, d1 represents a number in a range of 0 to 100; with the proviso that at least one R is $R^2$ when b1=0, and at least one R is $R^3$ when c1=0.

3. The silicone compound according to claim 1, wherein the "p" in the general formula (4) satisfies p=1.

4. The silicone compound according to claim 2, wherein the "p" in the general formula (4) satisfies p=1.

5. A cosmetic comprising the silicone compound according to claim 1.

6. A cosmetic comprising the silicone compound according to claim 2.

7. A cosmetic comprising the silicone compound according to claim 3.

8. A cosmetic comprising the silicone compound according to claim 4.

* * * * *